US009393233B2

(12) United States Patent
Anderson, Jr. et al.

(10) Patent No.: US 9,393,233 B2
(45) Date of Patent: Jul. 19, 2016

(54) VECTOR DELIVERY-BASED MICROBICIDES

(75) Inventors: Robert Anthony Anderson, Jr., Chicago, IL (US); Calvin J. Chany, II, Asbury, IA (US)

(73) Assignee: Rush University Medical Center, Chicago, IL (US)

( * ) Notice: Subject to any disclaimer, the term of this patent is extended or adjusted under 35 U.S.C. 154(b) by 1858 days.

(21) Appl. No.: 12/063,996

(22) PCT Filed: Aug. 14, 2006

(86) PCT No.: PCT/US2006/031631
§ 371 (c)(1),
(2), (4) Date: Sep. 10, 2010

(87) PCT Pub. No.: WO2007/022082
PCT Pub. Date: Feb. 22, 2007

(65) Prior Publication Data
US 2010/0331404 A1 Dec. 30, 2010

Related U.S. Application Data

(60) Provisional application No. 60/708,960, filed on Aug. 17, 2005.

(51) Int. Cl.
*A61K 9/00* (2006.01)
*A61K 31/19* (2006.01)
*A61K 31/192* (2006.01)
*A61K 31/21* (2006.01)
*A61K 31/215* (2006.01)
*A61K 31/216* (2006.01)
*A61K 31/4245* (2006.01)

(52) U.S. Cl.
CPC ........... *A61K 31/4245* (2013.01); *A61K 9/0034* (2013.01); *A61K 31/19* (2013.01); *A61K 31/192* (2013.01); *A61K 31/21* (2013.01); *A61K 31/215* (2013.01); *A61K 31/216* (2013.01)

(58) Field of Classification Search
CPC . A61K 31/4245; A61K 9/0034; A61K 31/19; A61K 31/192; A61K 31/21; A61K 31/215; A61K 31/216
See application file for complete search history.

(56) References Cited

U.S. PATENT DOCUMENTS

| 5,925,621 A | 7/1999 | Zaneveld et al. |
| 5,932,619 A | 8/1999 | Zaneveld et al. |
| 6,028,115 A | 2/2000 | Zaneveld et al. |
| 6,239,182 B1 | 5/2001 | Zaneveld et al. |

FOREIGN PATENT DOCUMENTS

WO  WO 96/02268  *  2/1996

OTHER PUBLICATIONS

Igietseme et al. 1997, "Inhibition of Intracellular multiplication of human strains of Chlamydia trachomatis by nitric oxide." Biochemical and Biophysical Research Communications, vol. 232, pp. 595-601.*
Endres et al. 1999, Eur. J. Med. Chem, vol. 34, pp. 895-901.*
Wang et al. Chem. Rev. 2002, 102, 1091-1134.*
Cirino Digestive and Liver Disease, 35 (Suppl. 2) 2003, S2-S8.*
Fang, F., "Mechanisms of Nitric Oxide-related Antimicrobial Activity," Journal of Clinical Investigation, Jun. 1997, p. 2818-2825, vol. 99, No. 12.
International Search Report, International Patent Application No. PCT/US2006/031631, Jul. 31, 2007, 1 Page.
Adler et al., "Suppression of herpes simplex virus type 1 (HSV-1)-induced pneumonia in mice by inhibition of inducible nitric oxide synthase (iNOS, NOS2)," J. Exp. Med, 185: 1533-40 (1997).
Allaker et al., "Antimicrobial effect of acidified nitrite on periodontal bacteria," Oral Microbiol. Immunol. 16: 253-6 (2001).
Anderson et al. "Evaluation of poly(styrene-4-sulfonate) as a preventive agent for conception and sexually transmitted diseases," J Androl 21:862-875 (2000).
Anderson et al., "Preclinical evaluation of sodium cellulose sulfate (Ushercell™) as a contraceptive antimicrobial agent," J. Androl. 23: 426-38 (2002).
Anderson et al., "SAMMA induces premature acrosomal loss by Ca$^{2+}$ signaling dysregulation," J. Androl. 27: 568-577 (2006).
Azenabor et al., "*Chlamydia pneumoniae* survival in macrophages is regulated by free Ca$^{2+}$ dependent reactive nitrogen and oxygen species," J. Infect. 46: 120-8 (2003).
Benencia et al., "Effect of aminoguanidine, a nitric oxide synthase inhibitor, on ocular infection with herpes simplex virus in Balb/c mice," Invest. Opthalmol. Vis. Sci. 42: 1277-84 (2001).
Benencia et al, "Nitric oxide and HSV vaginal infection in BALB/c mice," Virology 309: 75-84 (2003).
Benencia et al., "Nitric oxide and macrophage antiviral extrinsic activity," Immunology 98: 363-70 (1999).
Benz et al., "Tonal nitric oxide and health: antibacterial and viral actions and implications for HIV," Med. Sci Monitor. 8: RA27-RA31 (2002).
Bertinaria et al. ("Synthesis and anti-*Helicobacter pylori* properties of NO-donor/metronidazole hybrids and related compounds," Drug Devel. Res. 60: 225-39, (2003).
Bogdan, "Reactive oxygen and reactive nitrogen metabolites as effector molecules against infectious pathogens," in *The innate immune response to infection* (Kaufmann et al., eds.), Washington, D.C.: ASM Press, p. 357-96 (2004).

(Continued)

*Primary Examiner* — Kara R McMillian
(74) *Attorney, Agent, or Firm* — Brinks Gilson & Lione

(57) ABSTRACT

A new class of anti-microbial agents and methods for preventing or reducing the risk of sexually transmitted infections and/or diseases is provided. Preferably, these anti-microbial agents are also contraceptive and, thus, also prevent or reduce the risk of unplanned pregnancies. The anti-microbial agents comprise a delivery vector having anti-microbial activity (and preferably contraceptive activity) coupled with a nitric oxide donor moiety.

14 Claims, 4 Drawing Sheets

(56) References Cited

OTHER PUBLICATIONS

Broillet, "S-nitrosylation of proteins," Cell Mol. Life. Sci. 55: 1036-42 (1999).
Bussiere et al., "Spermine causes loss of innate immune response to *Helicobacter pylori* by inhibition of inducible nitric-oxide synthase translation," J. Biol. Chem. 280: 2409-12 (2005).
Campos-Perez et al., "Toxicity of nitric oxide and peroxynitrite to bacterial pathogens of fish," Dis. Aquat. Org. 43: 109-15 (2000).
Canthaboo et al., "Investigation of role of nitric oxide in protection from *Bordetella pertussis* respiratory challenge," Infect. Immun. 70: 679-84 (2002).
Carryn et al., "Impairment of growth of *Listeria monocytogenes* in THP-1 macrophages by granulocyte macrophage colony-stimulating factor: release of tumor necrosis factor-alpha and nitric oxide," J. Inf. Dis. 189: 2101-9 (2004).
Chen et al., "Nitric oxide production: a mechanism of *Chlamydia trachomatis* inhibition in interferon-gamma-treated RAW264.7 cells," FEMS Immunol. Med. Microbiol. 14: 109-20 (1996).
Cheshenko et al., "Candidate Topical Microbicides Bind Herpes Simplex Virus Glycoprotein B and Prevent Viral Entry and Cell-to-Cell Spread," Antimicrob. Agent Chemother. 48: 2025-36 (2004).
Chesler et al.. "The role of IFN-gamma in immune responses to viral infections of the central nervous system," Cytokine Grth. Fact. Rev. 13: 441-54 (2002).
Clancy et al., "Nitric oxide sustains nuclear factor kappaB activation in cytokine-stimulated chondrocytes," Osteoarthrit. Cartil. 12: 552-558 (2004).
Copenhaver et al., "A mutant of *Mycobacterium tuberculosis* H37Rv that lacks expression of antigen 85A is attenuated in mice but retains vaccinogenic potential," Infect. Immun. 72: 7084-95 2004).
Cooper et al. ("*Chlamydia trachomatis* infection of human fallopian tube organ cultures," J. Gen. Microbiol. 136: 1109-15 (1990).
Corinti et al., "Regulatory role of nitric oxide on monocyte-derived dendritic cell functions," J. Interfer. Cytokine Res. 23: 423-431 (2003).
Croen, "Evidence for antiviral effect of nitric oxide. Inhibition of herpes simplex virus type 1 replication," J. Clin. Invest. 91: 2446-52 (1993).
Crouch et al., "Binding of fibronectin by *Trichomonas vaginalis* is influenced by iron and calcium," Microb. Pathogen. 31: 131-44 (2001).
De Jonge et al., "Synchronous assay for human sperm capacitation and the acrosome reaction," J. Androl. 10: 232-39 (1989).
Devitt et al., "Induction of alpha/beta interferon and dependent nitric oxide synthesis during *Chlamydia trachomatis* infection of McCoy cells in the absence of exogenous cytokine," Infect Immun 64: 3951-6 (1996).
Di Stilo et al., "New 1,4-Dihydropyridines Conjugated to Furoxanyl Moieties, Endowed with Both Nitric Oxide-like and Calcium Channel Antagonist Vasodilator Activities," J. Med. Chem. 41: 5393-401 (1998).
Diaz-Cazorla et al., "Dual effect of nitric oxide donors on cyclooxygenase-2 expression in human mesangial cells," J. Amer. Soc. Nephrol. 10: 943-952 (1999).
Dykhuizen et al., "Antimicrobial effect of acidified nitrite on gut pathogens: importance of dietary nitrate in host defense," Antimicrob. Agents Chemother. 40: 1422-5 (1996).
Ferioli et al., "A new class of furoxan derivatives as NO donors: mechanism of action and biological activity," J. Pharmacol. 114: 816-20 (1995).
Fiscus, "Involvement of cyclic GMP and protein kinase G in the regulation of apoptosis and survival in neural cells," Neurosig. 11: 175-90 (2002).
Freyholdt et al., "Beneficial effect of sodium nitroprusside after coronary artery bypass surgery: pump function correlates inversely with cardiac release of proinflammatory cytokines," J. Cardiovasc. Pharmacol. 42: 372-378 (2003).
Fruttero et al., "Unsymmetrically substituted furoxans. Part 11. Methylfuroxan-carbaldehydes," J. Heterocycl. Chem. 26: 1345-7 (1989).
Fujii et al., "Role of nitric oxide in pathogenesis of herpes simplex virus encephalitis in rats," Virology 256: 203-12 (1999).
Galley et al., "Regulation of nitric oxide synthase activity in cultured human endothelial cells: effect of antioxidants," Free Rad. Biol. Med. 21: 97-101 (1996).
Gradoni et al., "Nitric oxide and anti-protozoan chemotherapy," Parassitologia. 46: 101-3 (2004). Abstract Only.
Gross et al., "Nitric oxide: pathophysiological mechanisms," Ann. Rev. Physiol. 57: 737-69 (1995).
Haider et al., "Dual functionality of cyclooxygenase-2 as a regulator of tumor necrosis factor-mediated G1 shortening and nitric oxide-mediated inhibition of vascular smooth muscle cell proliferation," Circulation 108: 1015-1021 (2003).
Herold et al., "Mandelic acid condensation polymer: novel candidate microbicide for prevention of human immunodeficiency virus and herpes simplex virus entry," J. Virol. 76: 11236-44 (2002).
Herrero et al., "Evidence that nitric oxide synthase is involved in progesterone-induced acrosomal exocytosis in mouse spermatozoa," Reprod. Fertil. Develop. 9: 433-9 (1997).
Herrero et al., "Nitric oxide interacts with the cAMP pathway to modulate capacitation of human spermatozoa," Free Rad. Biol. Med. 29: 522-36 (2000).
Herrero et al., "Progesterone enhances prostaglandin E2 production via interaction with nitric oxide in the mouse acrosome reaction," Biochem. Biophys. Res. Commun.; 252: 324-8 (1998).
Heywood et al., "Nicorandil inhibits degranulation and TNF-alpha release from RBL-2H3 cells," Inflam. Res. 51: 176-181 (2002).
Hickman-Davis et al., "Cyclophosphamide decreases nitrotyrosine formation and inhibits nitric oxide production by alveolar macrophages in mycoplasmosis," Inf. lmmun. 69: 6401-10 (2001).
Hickman-Davis et al., "Surfactant protein A mediates mycoplasmacidal activity of alveolar macrophages by production of peroxynitrite," Proc. Nat. Acad. Sci. USA 96: 4953-8 (1999).
Igietseme et al., "Inhibition of intracellular multiplication of human strains of *Chlamydia trachomatis* by nitric oxide," Biochem. Biophys. Res. Commun. 232: 595-601 (1997).
Igietseme "Molecular mechanism of T-cell control of *Chlamydia* in mice: role of nitric oxide in vivo," Immunology 88: 1-5 (1996).
Igietseme, "The molecular mechanism of T-cell control of *Chlamydia* in mice: role of nitric oxide," Immunology 87: 1-8 (1996).
Jiang et al., "Effects of antioxidants and NO on TNF-alpha-induced adhesion molecule expression in human pulmonary microvascular endothelial cells," Resp. Med. 99: 580-91 (2005).
Johansson et al., "Genital tract infection with *Chlamydia trachomatis* fails to induce protective immunity in gamma interferon receptor-deficient mice despite a strong local immunoglobulin A response," Inf. Immun. 65: 1032-44 (1997).
Karupiah et al., "Inhibition of viral replication by nitric oxide and its reversal by ferrous sulfate and tricarboxylic acid cycle metabolites," J. Exp. Med. 181: 2171-9 (1995).
Keller et al., "Rigorous pre-clinical evaluation of topical microbicides to prevent transmission of human immunodeficiency virus," J. Antimicrob. Chemother. 51: 1099-1102 (2003).
Keller et al., "Topical microbicides for the prevention of genital herpes infection," J. Antimicrob. Chemother. 55: 420-423 (2005).
Kelley et al., "Synthesis of bis(arylsulfonyl)furoxans from aryl nitromethyl sulfones," J. Heterocycl. Chem. 14: 1415-6 (1977).
Kerr et al., "Nitric oxide exerts distinct effects in local and systemic infections with *Streptococcus pneumoniae*," Microb. Pathogen. 36: 303-10 (2004).
Kodukula et al., "Macrophage control of herpes simplex virus type 1 replication in the peripheral nervous system," J. Immunol. 162: 2895-905 (1999).
Kurjak et al., "NO releases bombesin-like immunoreactivity from enteric synaptosomes by cross-activation of protein kinase A," Amer. J. Physiol. 276: G1521-G30 (1999).
Kwak et al., "Molsidomine ameliorates experimental allergic encephalomyelitis in Lewis rats," Immunopharmacol. Immunotoxicol. 25: 41-52 (2003).

(56) References Cited

OTHER PUBLICATIONS

Lagente et al., "A nitric oxide-releasing salbutamol elicits potent relaxant and anti-inflammatory activities," J. Pharmacol. Exp. Ther. 310: 367-375 (2004).
Ledingham et al., "Nitric oxide donors stimulate prostaglandin F(2 alpha) and inhibit thromboxane B(2) production in the human cervix during the first trimester of pregnancy," Mol. Hum. Reprod. 5: 973-982 (1999).
Lee et al., "Exogenous nitric oxide inhibits tumor necrosis factor-alpha- or interleukin-1-beta-induced monocyte chemoattractant protein-1 expression in human mesangial cells. Role of IkappaB-alpha and cyclic GMP," Nephron 92: 780-787 (2002).
Leib et al., "Inducible nitric oxide synthase and the effect of aminoguanidine in experimental neonatal meningitis," J. Inf. Dis. 177: 692-700 (1998).
Lolli et al., "A new class of ibuprofen derivatives with reduced gastrotoxicity," J. Med. Chem. 44: 3463-8 (2001).
Lusitani et al., "*Borrelia burgdorferi* are susceptible to killing by a variety of human polymorphonuclear leukocyte components," J. Infect. Dis. 185: 797-804 (2002).
MacLean et al, "Mice lacking inducible nitric-oxide synthase are more susceptible to herpes simplex virus infection despite enhanced Th1 cell responses," J. Gen. Virol. 79: 825-30 (1998).\.
Macphail et al., "Nitric oxide regulation of human peripheral blood mononuclear cells: critical time dependence and selectivity for cytokine versus chemokine expression," J. Immunol. 171: 4809-4815 (2003).
Mayer et al., "Gamma interferon-induced nitric oxide production reduces *Chlamydia trachomatis* infectivity in McCoy cells," Infect. Immun. 61: 491-7 (1993).
Medana et al., "Furoxans as Nitric Oxide Donors. 4-Phenyl-3-furoxancarbonitrile: Thiol-Mediated Nitric Oxide Release and Biological Evaluation," J. Med. Chem. 37: 4412-6 (1994).
Minin and Walton ("Radical Ring Closures of 4-Isocyanato Carbon-Centered Radicals," J. Org. Chem. 68: 2960-3 (2003).
Myers et al., "Localized reactive oxygen and nitrogen intermediates inhibit escape of *Listeria monocytogenes* from vacuoles in activated macrophages," J. Immunol. 171: 5447-53 (2003).
Nablo et al., "Nitric oxide-releasing sol-gels as antibacterial coatings for orthopedic implants," Biomaterials 26: 917-24 (2005).
Niinobu et al., "Negative feedback regulation of activated macrophages via Fas-mediated apoptosis," Amer. J. Physiol. 279: C504-0509 (2000).
Ofek et al., "Adhesins, receptors, and target substrata involved in the adhesion of pathogenic bacteria to host cells and tissues," in *Bacterial adhesion to animal cells and tissues*, Washington, D.C.: ASM Press, p. 177-405 (2003).
Ozturk et al., "Serum and mucosal nitric oxide levels and efficacy of sodium nitroprusside in experimentally induced acute sinusitis," Yonsei. Med. J. 44: 424-8 (2003).
Paludan et al., "Interferon (IFN)-gamma and Herpes simplex virus/tumor necrosis factor-alpha synergistically induce nitric oxide synthase 2 in macrophages through cooperative action of nuclear factor-kappa B and IFN regulatory factor-1," Eur. Cytokine Netw. 12: 297-308 (2001).
Persichini et al., "Cysteine nitrosylation inactivates the HIV-1 protease," Biochem. Biophys. Res Commun. 250: 575-6 (1998).
Persichini et al., "Molecular bases for the anti-HIV-1 effect of NO. Commentary," Int. J. Mol. Med. 4: 365-8 (1999).
Persichini, et al., "Nitric oxide inhibits the HIV-1 reverse transcriptase activity," Biochem. Biophys. Res. Commun. 258: 624-7 (1999).
Potter et al., "Exogenous nitric oxide inhibits apoptosis in guinea pig gastric mucous cells," Gut 46: 156-62 (2000).
Proud, "Nitric oxide and the common cold," Cur. Opin. Allergy Clin. Immunol. 5: 37-42 (2005).
Puliti et al., "Inhibition of nitric oxide synthase exacerbates group B *streptococcus* sepsis and arthritis in mice," Inf. Immun. 72: 4891-4 (2004).
Rachlis et al., "Nitric oxide reduces bacterial superantigen-immune cell activation and consequent epithelial abnormalities," J. Leukocyte Biol. 72: 339-346 (2002).
Ramsey et al., "*Chlamydia trachomatis* persistence in the female mouse genital tract: inducible nitric oxide synthase and infection outcome," Infect. Immun. 69: 5131-7 (2001).
Ramsey et al., "Role for inducible nitric oxide synthase in protection from chronic *Chlamydia trachomatis* urogenital disease in mice and its regulation by oxygen free radicals," Inf. Immun. 69: 7374-9 (2001).
Remer et al., "Nitric oxide is protective in listeric meningoencephalitis of rats," Inf. Immun. 69: 4086-93 (2001).
Revelli et al., "Follicular fluid proteins stimulate nitric oxide (NO) synthesis in human sperm: a possible role for NO in acrosomal reaction," J. Cell Physiol. 178: 85-92 (1999).
Revelli et al., "Signaling pathway of nitric oxide-induced acrosome reaction in human spermatozoa", Biol. Reprod., 64: 1708-12 (2001).
Rodriguez-Pena et al., "Intrarenal administration of molsidomine, a molecule releasing nitric oxide, reduces renal ischemia-reperfusion injury in rats," Amer. J. Transplant. 4: 1605-1613 (2004).
Saavedra et al., "The secondary amine/nitric oxide complex ion $R_2N[N(O)NO]$ as nucleophile and leaving group in S(N)Ar reactions," J. Org. Chem. 66: 3090-8 (2001).
Sales et al., "Nitric oxide supplementation ameliorates dextran sulfate sodium-induced colitis in mice," Lab. Invest. 82: 597-607 (2002).
Sander and Cramer ("A practical method for testing the spermicidal action of chemical contraceptives," Hum Fertil 6:134-137, 153 (1941).
Schonafinger, "Heterocyclic NO prodrugs," Farmaco. 54: 316-20 (1999).
Smeulders et al., "S-Nitrosoglutathione cytotoxicity to *Mycobacterium smegmatis* and its use to isolate stationary phase survival mutants," FEMS Microbiol. Lett. 239: 221-8 (2004).
Smolenski et al., "Functional analysis of cGMP-dependent protein kinases I and II as mediators of NO/cGMP effects," Naunyn-Schmied Arch. Pharmacol., 358: 134-139 (1998).
Soejima et al., "Preference toward a T-helper type 1 response in patients with coronary spastic angina," Circulation 107: 2196-2200 (2003).
Sorba et al., "Unsymmetrically substituted furoxans. Part 16. Reaction of benzenesulfonyl substituted furoxans with ethanol and ethanethiol in basic medium," J. Heterocycl. Chem. 33: 327-34 (1996).
Stone, "Microbicides: a new approach to preventing HIV and other sexually transmitted infections," Nature Reviews 1: 977-85 (2002).
Torre et al., "Regulation of inflammatory responses to *Bordetella pertussis* by N(G)-monomethyl-L-arginine in mice intranasally infected," Mediat. Inflam. 8: 25-9 (1999).
Vila-Petroff et al., "Activation of distinct cAMP-dependent and cGMP-dependent pathways by nitric oxide in cardiac myocytes," Circul. Res. 84: 1020-31 (1999).
von Knethen et al., "NF-kappaB and AP-1 activation by nitric oxide attenuated apoptotic cell death in RAW 264.7 macrophages," Mol. Biol. Cell 10: 361-372 (1999).
Wong et al., "Cytokines, nitric oxide, and cGMP modulate the permeability of an in vitro model of the human blood-brain barrier," Exp. Neurol. 190: 446-455 (2004).
Xiong et al., "Inhibition of interleukin-12 p40 transcription and NF-kappaB activation by nitric oxide in murine macrophages and dendritic cells," J. Biol. Chem. 279: 10776-10783 (2004).
Yamashiro et al., "Lower expression of Th1-related cytokines and inducible nitric oxide synthase in mice with streptozotocin-induced diabetes mellitus infected with *Mycobacterium tuberculosis*," Clin. Exp. Immunol. 139: 57-64 (2005).
Zaneveld et al., "Use of mandelic acid condensation polymer (SAMMA), a new antimicrobial contraceptive agent, for vaginal prophylaxis," Fertil. Ster. 78: 1107-15 (2002).
Zhang et al., "Differential antibacterial activity of nitric oxide from the immunological isozyme of nitric oxide synthase transduced into endothelial cells," Nitric Oxide 7: 42-9 (2002).

\* cited by examiner

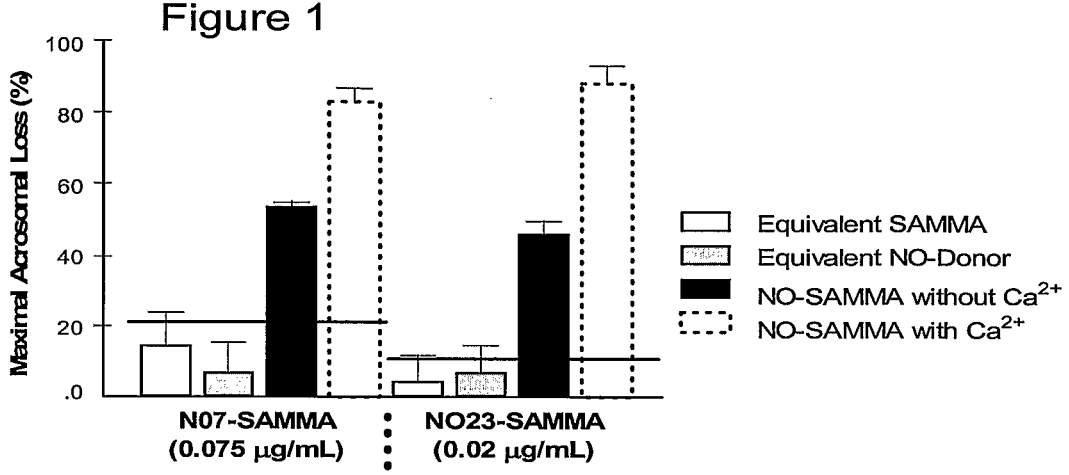
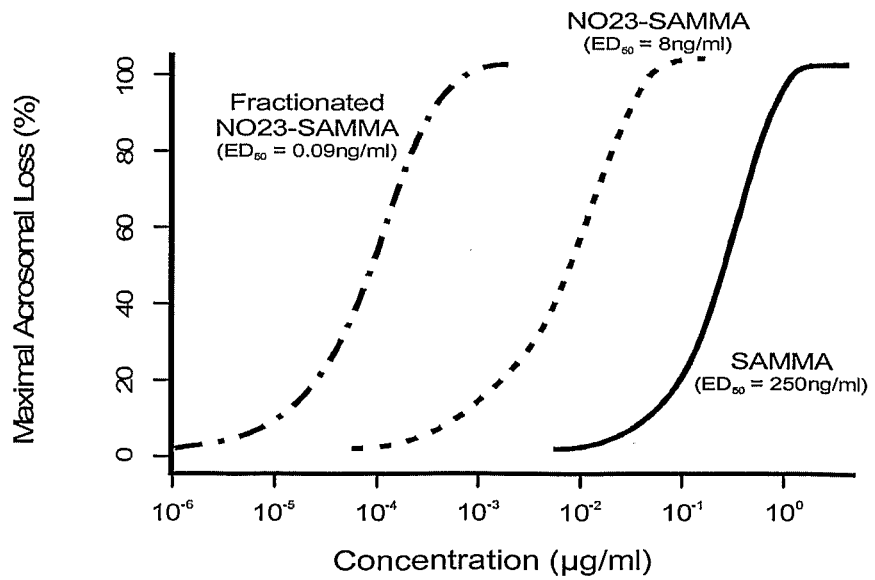

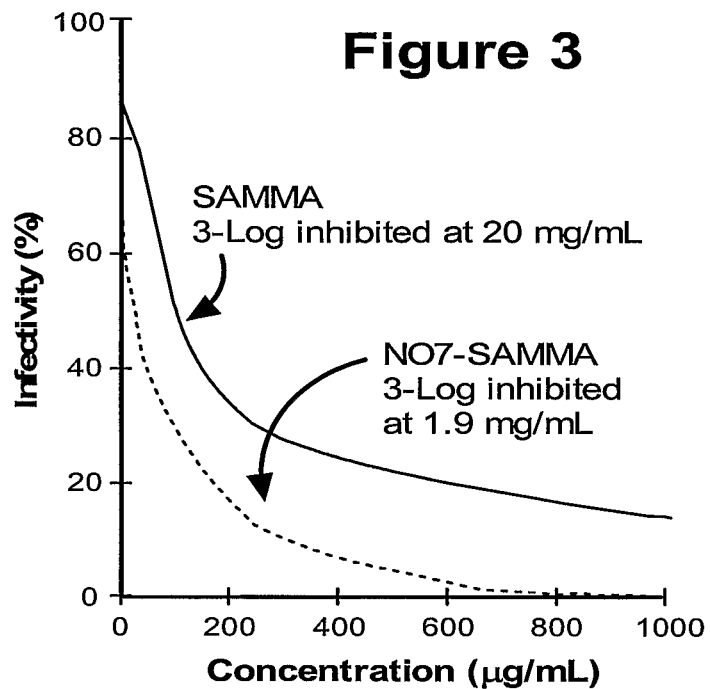
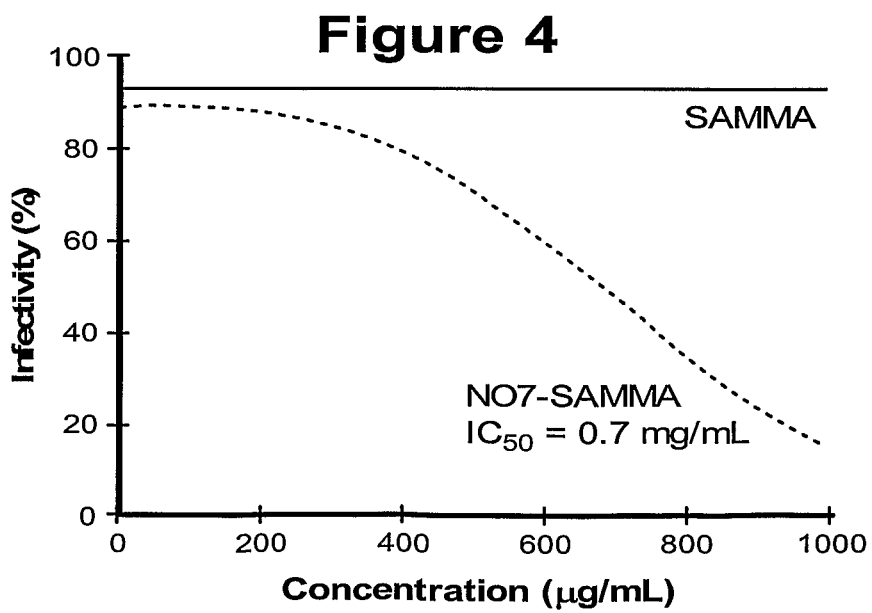

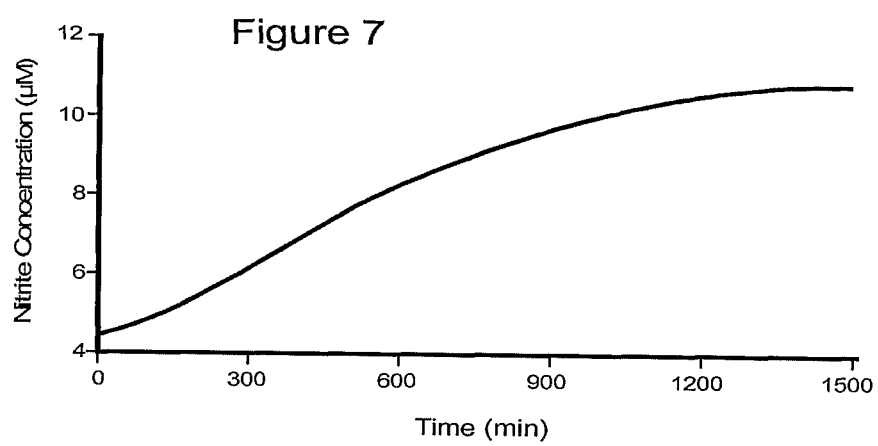

VECTOR DELIVERY-BASED MICROBICIDES

RELATED APPLICATION

This application is the National Stage of International Application No. PCT/US2006/031631, published in English under PCT Article 21(2), filed Aug. 14, 2006, which claims the benefit of U.S. Provisional Application Ser. No. 60/708,960, filed on Aug. 17, 2005, both of which are incorporated by reference in their entirety.

GOVERNMENT SPONSORED RESEARCH

This invention was made with government support under grant number HD041763 awarded by the National Institutes of Health. The government has certain rights in the invention.

FIELD OF THE INVENTION

This invention generally relates to a new class of anti-microbial agents and methods for preventing or reducing the risk of sexually transmitted infections and/or diseases. Preferably, these anti-microbial agents are also contraceptive and, thus, also prevent or reduce the risk of unplanned pregnancies.

BACKGROUND OF THE INVENTION

In recent years, sexually transmitted diseases have become an increasing medical problem and concern throughout the world. The HIV/AIDS epidemic over the last decade or so has significantly and dramatically underscored the threat of STDs to the human population. Until there is a cure, or at least an effective treatment, the best, and perhaps only realistic, approach to this increasing problem of STDs (especially HIV/AIDS) appears to be reducing the risk of transmission of STDs by the STD-causing organisms and thus reducing the number of individuals who become newly infected. Even when treatments or cures become available, prevention of infections in the initial instance will likely remain as the first line of defense. For economic, medical, and psychological reasons, it is preferable to prevent the initial infection rather than treating, and even curing, individuals with STDs.

At present, education in regard to STDs, their modes of transmission, and so-called "safe-sex" techniques has, at least to some degree in the more developed countries, shown promise in reducing the risks of STD transmission through sexual activity. Screening of the blood supply has helped to reduce the risk of transmission of such STD-causing organisms via blood transfusions and related medical practices. Nonetheless, the spread of such STDs has not been halted to a satisfactory degree even in developed countries with active and progressive education programs. Even with their known effectiveness in preventing STDs, current safe-sex techniques are not always used, or are not always used properly, for many reasons (e.g., carelessness, lack of knowledge, improper techniques, cultural barriers, unplanned or spontaneous sexual activity, and the like). Moreover, even when used, safe-sex techniques (except perhaps abstinence) are not always effective. For example, condoms are generally only about 90 percent effective in preventing conception when used alone; in the case of such failures, STD-causing organisms, if present, may pass from one sexual partner to the other.

Various birth control devices—including barrier methods and vaginal contraceptives—are currently available. Some of these may, in addition, also have a least some degree of anti-STD activity. For example, condoms can help prevent the transmission of STDs so long as they are properly used and/or they perform properly. Nonoxynol-9, currently one of the most widely used contraceptive agents, is reported, at least in some cases, to reduce the risk of transmission of some STDs. Nonoxynol-9, which is a nonionic detergent with strong surfactant properties, acts, like most other chemical-based contraceptives, by killing or otherwise immobilizing spermatozoa (e.g., spermicidal activity). Nonoxynol-9 is a potent cytotoxic agent which tends to nonspecifically disrupt cell membranes. These properties, however, give rise to some very significant disadvantages. Because nonoxynol-9 is strongly cytotoxic, it can injure vaginal/cervical epithelial and other cells at concentrations as low as about 0.0005 percent. Clinical studies have confirmed epithelial disruption of the vagina and cervix. Nonoxynol-9 also disrupts the normal vaginal flora which provides a protective mechanism, perhaps by maintaining a low pH, to guard against the invasion of pathogenic microbes. Nonoxynol-9 may also partially dissolve or remove the protective glycoprotein coating in the vagina. The cytotoxic, flora-disruptive, and glycoprotein-removal effects of nonoxynol-9 can lead to vaginal damage or injury, including lesions. Some women are especially sensitive to nonoxynol-9 and manifest these effects with only occasional use. The disruption of these protective mechanisms by nonoxynol-9 can actually increase the risks of STD since the breakdown of the protective mechanisms, and especially the occurrence of lesions, allows STD-causing organisms an easier pathway into the cells. Thus, any anti-STD activity of the contraceptive may be reduced or even lost (i.e., overwhelmed) by the increased risk of infection due to physical damage from the contraceptive. Even if such a contraceptive method provided some degree of STD protection, it would, of course, mainly be directed at heterosexual relationships in which pregnancy was not desired.

More recently contraceptives having anti-STD activity have become available. U.S. Pat. No. 5,925,621 (Jul. 20, 1999), U.S. Pat. No. 5,932,619 (Aug. 3, 1999), U.S. Pat. No. 6,028,115 (Feb. 22, 2000), and U.S. Pat. No. 6,239,182 (May 29, 2001) provide methods for the reduction of sexual transmitted diseases using inhibitory agents such as phosphorylated hesperidins, sulfonated hesperidins, polystyrene sulfonates, substituted benzenesulfonic acid formaldehyde co-polymers, $H_2SO_4$-modified mandelic acids, and the like.

It would be desirable, therefore, to provide more effective anti-microbial agents and methods for preventing or reducing the risk of sexually transmitted infections and/or diseases; preferably such anti-microbial agents would also be contraceptive and, thus, prevent or reduce the risk of unplanned pregnancies. It would be desirable if such anti-microbial agents, whether contraceptive or not, and methods would not interfere with the natural and protective vaginal mechanisms. It would also be desirable if such anti-microbial agents, whether contraceptive or not, and methods would be relatively easy to use, have significantly fewer side effects than currently available methods (i.e., nonoxynol-9) so that it would more likely be used on a consistent basis, and be effective at lower concentrations. It would also be desirable if such anti-microbial agents, whether contraceptive or not, and methods could be used in heterosexual, homosexual, and bisexual relationships and for a wide range of sexual activities. It would also be desirable if such anti-microbial agents, whether contraceptive or not, and methods could be implemented by either party to the sexual activity. The present invention, as detailed in the present specification, provides such anti-microbial agents and contraceptive anti-microbial agents and methods.

SUMMARY OF THE INVENTION

This invention generally relates to improved anti-microbial agents and to methods for preventing STDs and/or reducing the risk of transmission of such STDs through sexual activity using the improved anti-microbial agents. Preferably, such anti-microbial agents are also contraceptive. The anti-microbial agents comprise a delivery vector having anti-microbial activity (and preferably contraceptive activity) coupled with a nitric oxide donor moiety. The method is suitable for use by heterosexual, homosexual, and bisexual individuals to significantly reduce the risk of being infected by, or of transmitting, a STD through sexual contact. Moreover, the risk of pregnancy during heterosexual activity is also significantly reduced in preferred embodiments. Although this method can be used alone, it is generally preferred that it be used in conjunction with other so-called "safe sex" techniques in order to even further reduce the risk of STD transmission or infection.

The method of this invention generally comprises the application of an effective amount of the improved anti-microbial agent or agents to the area or areas of sexual contact (e.g., genitalia) of at least one (and preferably all) of the participants prior to engaging in sexual activity. The anti-microbial agents of this invention comprises a delivery vector component having anti-microbial activity (and preferably contraceptive activity) coupled with a nitric oxide donor moiety. For purposes of this invention the "anti-microbial agent" is a compound or mixture of compounds which can inactivate at least one major STD-causing organisms (HIV, HSV, gonococci, papilloma virus, and/or chlamydia) without necessarily killing them and which generates nitric oxide in situ (i.e., at the binding site of the delivery vector component). The nitric oxide, thus released, can kill or otherwise inactivate the microbe; the microbe can also be killed or otherwise inactivated by the delivery vector component. "Anti-microbial agents" of this invention may or may not (but preferably do) have contraceptive activity in addition to the anti-microbial activity. Vector delivery components which are preferred in the present invention for preparing anti-microbial agents are inhibitory agents such as phosphorylated hesperidins, sulfonated hesperidins, polystyrene sulfonates, substituted benzenesulfonic acid formaldehyde co-polymers, $H_2SO_4$-modified mandelic acids, cellulose sulfates, and the like. Thus, preferred NO-coupled anti-microbial agents of this invention include, for example, phosphorylated hesperidins coupled with a NO-donor, sulfonated hesperidins coupled with a NO-donor, polystyrene sulfonates coupled with a NO-donor, substituted benzenesulfonic acid formaldehyde co-polymers coupled with a NO-donor, $H_2SO_4$-modified mandelic acids coupled with a NO-donor, and cellulose sulfates coupled with a NO-donor, and the like. Preferably the vector delivery components as well as the NO-coupled anti-microbial agents used in the present invention are at least partially water soluble or water dispersable so that anti-STD formulations can more easily be prepared. More preferred anti-microbial agents for use in this invention include $H_2SO_4$-modified mandelic acids (SAMMAs) coupled with a NO-donor (i.e., NO-SAMMAs). Preferred NO-SAMMAs include those which have been fractionated so as to have a narrower molecular weight distribution and increased activities.

In addition to anti-STD activity, these compounds may also act as vaginal contraceptives (and preferably do act as such) and generally have fewer side effects than conventional vaginal contraceptives (e.g., nonoxynol-9). For example, the compounds useful in this invention are generally not toxic (or only minimally toxic) to natural and beneficial vaginal flora and, thus, do not significantly upset the local microbiological balance or significantly disrupt the protective glycoprotein vaginal coating. Disruption of the natural vaginal flora and/or removal or disruption of the protective glycoprotein vaginal coating using conventional vaginal contraceptives can lead to irritation of the vaginal wall and/or lesions on the vaginal wall which can make the transmission of STD easier and/or more likely. In addition, the compounds useful in this invention are generally not disruptive to rectal tissue and should not, therefore, significantly contribute to the formation of lesions or breaks in the rectal lining which could increase the risk of STD transmission during anal intercourse. Moreover, the anti-microbial agents of the present invention, largely due to their dual activities and site-specific delivery of nitric oxide, can be used at lower concentrations, thereby reducing the risk of side effects or other adverse effects.

Either party to the sexual contact can employ the method of the present invention in order to protect him or herself and their partners. This feature allows either party to take protective measures without relying on the motivation or action of the other party. Of course, the highest level of protection is obtained when both or all parties take appropriate steps to practice the methods of this invention in conjunction with "safe-sex" techniques.

BRIEF DESCRIPTION OF THE DRAWINGS

FIG. 1 is a plot of percentage maximal acrosomal loss of NO7-SAMMA and NO23-SAMMA in the presence and absence of $Ca^{2+}$ as well as their respective vector and NO-donor alone. The error bars represent 90% confidence limits. The bold horizontal lines in the chart area represent the predicted responses to NO7-SAMMA and NO23-SAMMA, respectively, assuming independence of the equivalent NO-donor and SAMMA responses in the presence of $Ca^{2+}$.

FIG. 2 is a comparison of SAMMA, NO23-SAMMA, and fractionated NO23-SAMMA as acrosomal loss stimuli.

FIG. 3 is a comparison of SAMMA and NO7-SAMMA for *C. trachomatis* inhibition. Elementary bodies were preincubated with agent (either SAMMA or NO7-SAMMA) for 4 hours at 0° C. before inoculation onto HeLa cells.

FIG. 4 is another comparison of SAMMA and NO7-SAMMA for *C. trachomatis* inhibition. HeLa cells were preincubated with agent (either SAMMA or NO7-SAMMA) for 4 hours at 37° C. before inoculation.

FIG. 7 illustrates nitrite release from fractionated NO23-SAMMA in the presence of 50 mM L-cysteine.

DETAILED DESCRIPTION OF THE INVENTION

Figure 5:
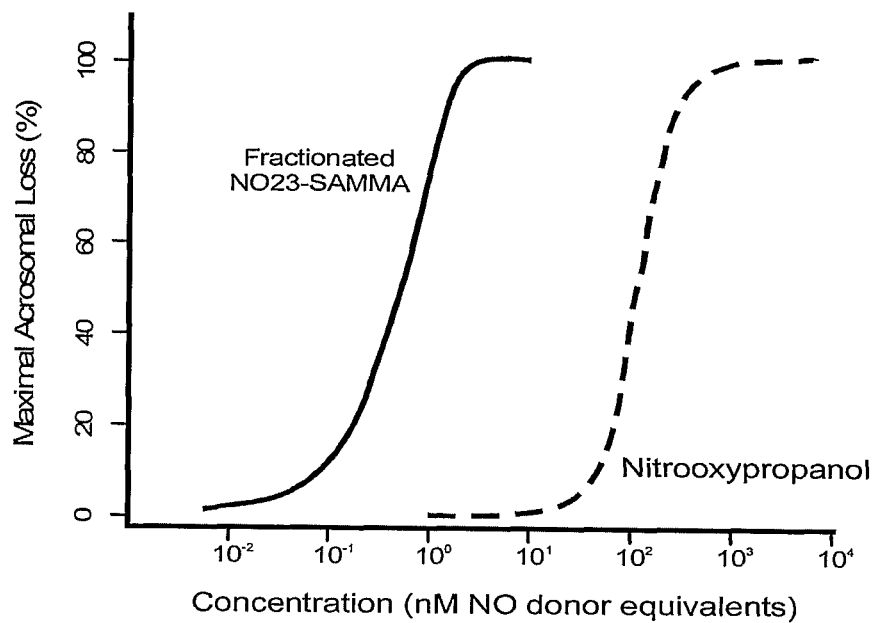
FIG. 5 is a comparison of fractionated NO23-SAMMA and nitrooxypropanol as acrosomal loss stimuli in the absence of $Ca^{2+}$; thus, the activity of fractionated NO23-SAMMA is due to the NO donor moiety.

This invention generally relates to improved anti-microbial agents and to methods for preventing STDs and/or reducing the risk of transmission of such STDs through sexual activity using the improved anti-microbial agents. The anti-microbial agents comprises a delivery vector having anti-microbial activity, and preferably contraceptive activity, coupled with a nitric oxide donor moiety. The vector delivery component is designed to have affinity toward surface receptors required for target cell recognition by spermatozoa (oocytes) and/or pathogenic microbes (susceptible tissue). It provides a vector-mediated targeted delivery of NO, a naturally occurring, biologically active compound with known activities against spermatozoa and pathogenic microbes, including, though not restricted to, HIV, HSV, and *C. trachomatis*. NO is produced in situ by the NO donor covalently attached to the vector. The anti-microbial agent is expected to bind with the targeted surface receptors on spermatozoa and/or pathogenic microbes; once bound, released NO can effect its known activities against the spermatozoa and/or pathogenic microbes in a very effective manner. Indeed, lower concentrations of the anti-microbial agent will be effective since delivery of the NO to the target organisms combined with the inherent activity of the vector delivery component will be much more effective as compared to either the vector component alone or NO donor alone.

The preferred contraceptive antimicrobial agents of this invention are especially intended to prevent sexually transmitted infections and unplanned pregnancies. However, they may also have utility in preventing blood-borne pathogenic microbes from entering surrounding tissues. NO-coupled $H_2SO_4$-modified mandelic acids (NO-SAMMAs) are prototypes of this type of agent. They act by multiple mechanisms. They provide a vector-mediated targeted delivery of NO, a naturally occurring, biologically active compound with known activities against spermatozoa and pathogenic microbes, including, though not restricted to, HIV, HSV, and *C. trachomatis*. NO is produced by a NO donor covalently attached to the vector. The vector can be any one of several compounds with affinity toward surface receptors required for target cell recognition by spermatozoa (oocytes) and pathogenic microbes (susceptible tissue). Examples of receptors on pathogenic microbes are collectively known as adhesins. Examples of receptors on spermatozoa have affinity toward oocyte-related proteins, such as the zona pellucida, and are collectively known as heparin (or glycosaminoglycan) binding proteins or lectins. The vector is a ligand for these receptors.

Both vector and released NO contribute to its activity, each by one or more mechanisms. The combination of these moieties on the same molecule is more effective than either of the separate parts used alone, or in combination. This applies to the contraceptive and anti-microbial activities of these agents, possibly by different mechanisms. The vector (ligand) promotes NO formation and biological activity in responsive cells, including spermatozoa, by a mechanism independent from that due to the NO donor. The response is synergistic to the expected response to the NO donor and ligand added in combination. The method of NO delivery provided by these new agents is more effective than would be provided by the NO donor alone. The ligand portion of the molecule binds directly to the spermatozoon or pathogenic microbe. NO released from the agent is in direct contact with the cell, allowing lower concentrations to accomplish the same effect as the NO donor alone.

These new agents are expected to be more effective against pathogenic microbes than the ligand or NO donor used alone or in combination. Activity of NO-SAMMA against *C. trachomatis* supports this contention. The ligand is classified as an entry inhibitor. Entry inhibitors provide protection against microbial invasion of susceptible cells, but probably have little beneficial effect against microbial survival or replication. NO-SAMMA and similar compounds increase the effectiveness of the ligand by providing a means of killing or otherwise inactivating the microbe through the release of NO. Adhesin-like receptors have also been identified on potential target cells for microbial invasion. NO produced in these cells in response to interaction with NO-SAMMA and related compounds could contribute to their anti-microbial activities.

Moreover, these new agents are expected to have broad anti-microbial activity since the basic activity of the delivery vector component and the released NO are present even in cases where the synergistic effects noted above may be absent. For example, not all microbes are sensitive to NO. Thus, while NO-SAMMA does not offer enhanced activity against *N. gonorrhoeae*, the activity against this microbe due to SAMMA alone remains. In other words, microbes do not have to be sensitive to both NO and the adhesin receptor antagonist to be affected by the anti-microbial compounds of this invention. Of course, sensitivity to both NO and the adhesin receptor antagonist results in significantly increased kill or inhibition rates.

Preferred vector delivery components which are useful in the present invention for preparing anti-microbial agents are inhibitory agents such as phosphorylated hesperidins, sulfonated hesperidins, polystyrene sulfonates, substituted benzenesulfonic acid formaldehyde co-polymers, $H_2SO_4$-modified mandelic acids, cellulose sulfates, and the like. Thus, preferred NO-coupled anti-microbial agents of this invention include, for example, phosphorylated hesperidins coupled with a NO-donor, sulfonated hesperidins coupled with a NO-donor, polystyrene sulfonates coupled with a NO-donor, substituted benzenesulfonic acid formaldehyde co-polymers coupled with a NO-donor, $H_2SO_4$-modified mandelic acids coupled with a NO-donor, cellulose sulfates coupled with a NO-donor, and the like. Preferably the vector delivery components as well as the NO-coupled anti-microbial agents used in the present invention are at least partially water soluble or water dispersable so that anti-STD formulations can more easily be prepared. Especially preferred anti-microbial agents for use in this invention include $H_2SO_4$-modified mandelic acids (SAMMAs) coupled with a NO-donor (i.e., NO-SAMMAs).

As noted above, preferred NO-SAMMAs include those which have been fractionated so as to have a narrower molecular weight distribution and increased activities (as measured against unfractionated material). It is expected that the preparation of other NO-coupled anti-microbial agents having narrower molecular weight distributions will also have increased activities relative to their unfractionated counterparts. Such narrower molecular weight distributions can be obtained by fractionating the starting materials (e.g., SAMMA) or the final products (e.g., NO-SAMMA) using conventional separation techniques; generally, it is preferred that the starting materials be fractionated. Although not wishing to be limited by theory, it appears that the intermediate molecular weight materials may have higher binding affinities for relevant biological materials and thus higher activities. Of course, the optimal molecular weight range for a given NO-coupled anti-microbial agent can be determined by routine experimentation. Moreover, the optimal molecular weight range of a given NO-coupled antimicrobial agent may vary depending on the activity measured (e.g., contraceptive, acrosomal loss, anti-HIV, anti-HSV, and/or the like activities), the relative amount of NO coupled to the agent, and the like.

SAMMA (i.e., $H_2SO_4$-modified mandelic acid), the most preferred vector delivery component of this invention, is a carboxylated oligomer (average molecular weight of approximately 1.5 KDa) with contraceptive and antimicrobial properties. Generally, SAMMA has a distribution of carboxylated oligomers having from 2-3 repeating units up to 20 or more repeating units; typically the bulk of the material has 7-15 repeating units. Although not wishing to be limited by theory, it is thought that the reduction in the relative amounts of material having either low or high number of repeating unit by fractionation results in increased activities.

SAMMA is efficacious against HIV, HSV and *C. trachomatis*, among other sexually-transmitted pathogens. SAMMA is active against spermatozoa, inhibiting hyaluronidase and acrosin (two spermatozoal enzymes required for fertilization), causes premature acrosomal loss, and is contraceptive in the rabbit. (Zaneveld et al., "Use of mandelic acid condensation polymer (SAMMA), a new antimicrobial contraceptive agent, for vaginal prophylaxis," Fertil. Ster. 78: 1107-15 (2002); U.S. Pat. Nos. 5,925,621 (Jul. 20, 1999), 5,932,619 (Aug. 3, 1999), 6,028,115 (Feb. 22, 2000), and 6,239,182 (May 29, 2001).) However, sperm motility is unaffected by SAMMA at concentrations higher than those required for its antimicrobial and contraceptive activities, suggesting that it is not acting by killing spermatozoa. Similar findings have been made regarding its antimicrobial properties, insofar as minimal cytotoxic effects of SAMMA are seen on host cells used for microbial infection in vitro. (Herold et al., "Mandelic acid condensation polymer: novel candidate microbicide for prevention of human immunodeficiency virus and herpes simplex virus entry," J. Virol. 76: 11236-44 (2002).)

Although research on its mechanisms of action is ongoing, SAMMA's antiviral effects are thought to be mediated, at least in part, by its ability to antagonize viral binding to target cells, mediated by the viral adhesins gp120 (for HIV) and gB2 (for HSV). (Cheshenko et al., "Candidate Topical Microbicides Bind Herpes Simplex Virus Glycoprotein B and Prevent Viral Entry and Cell-to-Cell Spread," Antimicrob. Agent Chemother. 48: 2025-36 (2004); Herold et al., "Mandelic acid condensation polymer: novel candidate microbicide for prevention of human immunodeficiency virus and herpes simplex virus entry," J. Virol. 76: 11236-44 (2002).) SAMMA may be active against *C. trachomatis* by a similar mechanism. Post-adhesion interference with viral-mediated signal transduction at the level of the target cells remains to be determined.

SAMMA appears to induce premature acrosomal loss (AL) by a $Ca^{2+}$-dependent mechanism. Anderson et al., "SAMMA induces premature acrosomal loss by $Ca^{2+}$ signaling dysregulation," J. Androl. 27: 568-577 (2006). Although the initial point of interaction of SAMMA with spermatozoa (e.g., surface receptor(s)) is unknown, the process appears to require entry of extracellular $Ca^{2+}$. Unlike the physiological acrosome reaction, $Ca^{2+}$ entry is likely mediated by voltage-dependent T-type $Ca^{2+}$ channels (dose-dependent inhibition by diphenylhydantoin and $Ni^{2+}$), is unaffected by antagonism of InSP3 receptors, does not require release of intracellular $Ca^{2+}$ stores (not inhibited by 2-APB—an InSP3 receptor antagonist and blocker of store-operated $Ca^{2+}$ channels) and is not mediated by protein kinase A (not inhibited by KT5720, a selective protein kinase A inhibitor). SAMMA-induced acrosomal loss (SAL) requires protein kinase G and soluble guanylate cyclase (>95% inhibited by 2 μM KT5823—a selective protein kinase G inhibitor; ~50% inhibited by 0.1 μM ODQ—a selective inhibitor of soluble guanylate cyclase). Further, SAL is inhibited by inhibitors selective for the endothelial isoform of nitric oxide synthase. Taken together, these results suggest that SAL may be mediated by nitric oxide. Nitric oxide also likely mediates the acrosome reaction in response to physiological stimuli (e.g., progesterone and follicular fluid; Herrero et al., "Evidence that nitric oxide synthase is involved in progesterone-induced acrosomal exocytosis in mouse spermatozoa," Reprod. Fertil. Develop. 9: 433-9 (1997); Herrero et al., "Progesterone enhances prostaglandin E2 production via interaction with nitric oxide in the mouse acrosome reaction," Biochem. Biophys. Res. Commun.; 252: 324-8 (1998); Revelli et al., "Follicular fluid proteins stimulate nitric oxide (NO) synthesis in human sperm: a possible role for NO in acrosomal reaction," J. Cell Physiol. 178: 85-92 (1999); Herrero et al., "Nitric oxide interacts with the cAMP pathway to modulate capacitation of human spermatozoa," Free Rad. Biol. Med. 29: 522-36 (2000)).

The second component of the NO-SAMMAs of the present invention is a NO donor. NO donors alone also seem to induce AL, consistent with the proposed mechanism by which SAL occurs. However, unlike SAL, these reactions do not appear to require $Ca^{2+}$; the $Ca^{2+}$ requirement for SAL is likely upstream from the action of NO. Nor do they appear to require protein kinase G (not inhibited by 2 μM KT5823 or 0.35 μM Rp-8-Br-PET-cGMPS; Smolenski et al., "Functional analysis of cGMP-dependent protein kinases I and II as mediators of NO/cGMP effects," Naunyn-Schmied Arch. Pharmacol., 358: 134-139 (1998)). These results suggest that the same outcome (AL) is produced by the same biologically active intermediate (NO) produced by two stimuli/sources (SAMMA and NO-donors) by two independent mechanisms. Other work with NO-donors suggest that AL in response to these agents may be mediated by a cAMP-dependent mechanism. (Kurjak et al., "NO releases bombesin-like immunoreactivity from enteric synaptosomes by cross-activation of protein kinase A," Amer. J. Physiol. 276: G1521-G30 (1999); Vila-Petroff et al., "Activation of distinct cAMP-dependent and cGMP-dependent pathways by nitric oxide in cardiac myocytes," Circul. Res. 84: 1020-31 (1999).)

NO is a highly bioactive, short-lived gaseous molecule produced in response to various physiological stimuli. Among its actions are smooth muscle relaxation, inhibition of platelet aggregation and adhesion, neurotransmission, regulation of apoptosis, and cytotoxicity. Further, NO is toxic to a number of bacteria, viruses, and other foreign particles. (Gross et al., "Nitric oxide: pathophysiological mechanisms," Ann. Rev. Physiol. 57: 737-69 (1995).) Specifically, NO appear to play a key role in the natural defense against microbes, including HIV and HSV, and *Chlamydia*.

Viral enzymes (e.g., proteases, reverse transcriptases, ribonucleotide reductase) containing cysteine residues are targets for NO-mediated nitrosylation; viral-encoded transcription factors are also targets. (Persichini et al., "Cysteine nitrosylation inactivates the HIV-1 protease," Biochem. Biophys. Res Commun. 250: 575-6 (1998); Broillet, "S-nitrosylation of proteins," Cell Mol. Life. Sci. 55: 1036-42 (1999); Persichini et al., "Molecular bases for the anti-HIV-1 effect of NO. Commentary," Int. J. Mol. Med. 4: 365-8 (1999); Benz et al., "Tonal nitric oxide and health: antibacterial and viral actions and implications for HIV," Med. Sci Monitor. 8: RA27-RA31 (2002).) NO appears to react with and disrupt structural proteins essential for viral replication. (Saavedra et al., "The secondary amine/nitric oxide complex ion $R_2N[N(O)NO]^-$ as nucleophile and leaving group in S(N)Ar reactions," J. Org. Chem. 66: 3090-8 (2001).) Stimulus-induced NO production is beneficial in preventing HIV infection, and the protective effect of low levels of NO on cell survival in the CNS subsequent to HIV infection is recognized. (Fiscus, "Involvement of cyclic GMP and protein kinase G in the regulation of apoptosis and survival in neural cells," Neurosig. 11: 175-90 (2002).)

Endogenous or exogenous NO inhibits HSV-1 and HSV-2 infectivity. Agents lowering or antagonizing NO exacerbate HSV infection. Inducible nitric oxide synthase (iNOS) inhibition increases pathology and viral titers of HSV-2-infected mice. (Benencia et al., "Effect of aminoguanidine, a nitric oxide synthase inhibitor, on ocular infection with herpes simplex virus in Balb/c mice," Invest. Opthalmol. Vis. Sci. 42: 1277-84 (2001); Benencia et al., "Nitric oxide and HSV vaginal infection in BALB/c mice," Virology 309: 75-84 (2003). Macrophage iNOS activation forms part of the innate immune response to HSV. (Croen, "Evidence for antiviral effect of nitric oxide. Inhibition of herpes simplex virus type 1 replication," J. Clin. Invest. 91: 2446-52 (1993); Benencia et al., "Nitric oxide and macrophage antiviral extrinsic activity," Immunology 98: 363-70 (1999); Paludan et al., "Interferon (IFN)-gamma and Herpes simplex virus/tumor necrosis factor-alpha synergistically induce nitric oxide synthase 2 in macrophages through cooperative action of nuclear factor-kappa B and IFN regulatory factor-1," Eur. Cytokine Netw. 12: 297-308 (2001).) Macrophage NO inhibits HSV-1 replication, and iNOS inhibition increases HSV-1 titers. (Karupiah et al., "Inhibition of viral replication by nitric oxide and its reversal by ferrous sulfate and tricarboxylic acid cycle metabolites," J. Exp. Med. 181: 2171-9 (1995); Kodukula et al., "Macrophage control of herpes simplex virus type 1 replication in the peripheral nervous system," J. Immunol. 162: 2895-905 (1999).) iNOS-deficient knockout mice are more susceptible to HSV-1. (MacLean et al, "Mice lacking inducible nitric-oxide synthase are more susceptible to herpes simplex virus infection despite enhanced Th1 cell responses," J. Gen. Virol. 79: 825-30 (1998).) NOS inhibitors increase HSV-1-induced pathology. (Benencia et al., "Nitric oxide and macrophage antiviral extrinsic activity," Immunology 98: 363-70 (1999).) HSV elimination from the CNS requires NO. (Chesler et al., "The role of IFN-gamma in immune responses to viral infections of the central nervous system," Cytokine Grth. Fact. Rev. 13: 441-54 (2002).) iNOS-derived NO inhibits viral replication. (Benencia et al., "Effect of aminoguanidine, a nitric oxide synthase inhibitor, on ocular infection with herpes simplex virus in Balb/c mice," Invest. Opthalmol. Vis. Sci. 42: 1277-84 (2001); Kodukula et al., "Macrophage control of herpes simplex virus type 1 replication in the peripheral nervous system," J. Immunol. 162: 2895-905 (1999); Adler et al., "Suppression of herpes simplex virus type 1 (HSV-1)-induced pneumonia in mice by inhibition of inducible nitric oxide synthase (iNOS, NOS2)," J. Exp. Med. 185: 1533-40 (1997); Fujii et al., "Role of nitric oxide in pathogenesis of herpes simplex virus encephalitis in rats," Virology 256: 203-12 (1999).)

NO inhibits C. trachomatis growth. (Igietseme et al., "Inhibition of intracellular multiplication of human strains of Chlamydia trachomatis by nitric oxide," Biochem. Biophys. Res. Commun. 232: 595-601 (1997).) NO production by epithelial and possibly T-cells is important for the resolution of chlamydial infections. IFN-γ prevents C. trachomatis replication and promotes NO formation; both are inhibited by iNOS inhibitors. (Mayer et al., "Gamma interferon-induced nitric oxide production reduces Chlamydia trachomatis infectivity in McCoy cells," Infect. Immun. 61: 491-7 (1993); Devitt et al., "Induction of alpha/beta interferon and dependent nitric oxide synthesis during Chlamydia trachomatis infection of McCoy cells in the absence of exogenous cytokine," Infect Immun 64: 3951-6 (1996).) NO donors inhibit C. trachomatis replication in epithelial cells. (Igietseme et al., "Inhibition of intracellular multiplication of human strains of Chlamydia trachomatis by nitric oxide," Biochem. Biophys. Res. Commun. 232: 595-601 (1997).) Protection against chlamydial infection by T-cells correlates with their ability to induce NO production. (Igietseme, "The molecular mechanism of T-cell control of Chlamydia in mice: role of nitric oxide," Immunology 87: 1-8 (1996).) NOS inhibition increases bacterial titers of infected mice and impairs the ability of T-cell clones to clear genital chlamydial infection. (Igietseme, "Molecular mechanism of T-cell control of Chlamydia in mice: role of nitric oxide in vivo," Immunology 88: 1-5 (1996).) This is also seen in macrophages, with a strong correlation between NOS activity and chlamydial inhibition, effects antagonized by NOS inhibition. (Chen et al., "Nitric oxide production: a mechanism of Chlamydia trachomatis inhibition in interferon-gamma-treated RAW264.7 cells," FEMS Immunol. Med. Microbiol. 14: 109-20 (1996); Azenabor et al., "Chlamydia pneumoniae survival in macrophages is regulated by free $Ca^{2+}$ dependent reactive nitrogen and oxygen species," J. Infect. 46: 120-8 (2003).) Mouse strains that produce more NO are more resistant to C. trachomatis. (Ramsey et al., "Role for inducible nitric oxide synthase in protection from chronic Chlamydia trachomatis urogenital disease in mice and its regulation by oxygen free radicals," Inf. Immun. 69: 7374-9 (2001).) Macrophages from chlamydia-infected, IFN-γ receptor-deficient mice have increased chlamydial titers, and no detectable NO. (Johansson et al., "Genital tract infection with Chlamydia trachomatis fails to induce protective immunity in gamma interferon receptor-deficient mice despite a strong local immunoglobulin A response," Inf. Immun. 65: 1032-44 (1997).) In iNOS-deficient mice, IFN-γ is bacteriostatic against chlamydial infection. However, IFN-γ is bactericidal in iNOS-sufficient mice and eradicates the microbe. (Ramsey et al., "Chlamydia trachomatis persistence in the female mouse genital tract: inducible nitric oxide synthase and infection outcome," Infect. Immun. 69: 5131-7 (2001).)

The present invention, in an especially preferred form, combines SAMMA and a NO donor in a single compound or molecule which provides the benefits of both components in a synergistic manner. As noted above, (1) SAL occurs by a $Ca^{2+}$- and NO-dependent mechanism; (2) NO release from NO donors induces AL by a $Ca^{2+}$-independent mechanism, distinct from that responsible for SAL; and (3) NO has antiviral and antibacterial activities, and has a key role in the natural defense against HIV, HSV and C. trachomatis infections. It was hoped that both the contraceptive and antimicrobial activities of SAMMA could be improved through the covalent attachment of an NO donor. This has proven to be the case; indeed the degree of improvement has been surprising.

The NO-SAMMA compound of the present invention was found to have the following properties: (1) induces AL in the presence or absence of $Ca^{2+}$; (2) AL due to NO release (in the absence of $Ca^{2+}$) is effected by a lower concentration of NO-donor equivalents present in the derivative than required for NO-donor alone (not wishing to be limited by theory, this effect is thought to be largely due to the fact that the source of NO would be directed to the surface of the target cell); (3) activity of the derivative against spermatozoa is synergistic compared with either NO-donor or SAMMA alone (again, not wishing to be limited by theory, this effect is thought to be due to different mechanisms by which they induce AL); (4) antimicrobial activity due to NO release occurs at lower concentration of NO-donor equivalents present in the derivative than required for NO donor alone; and (5) a synergistic antimicrobial effect compared to either NO-donor or SAMMA alone has been found. It appears that the SAMMA moiety inhibits microbial binding to target or host cells and the NO produced by the NO-donor moiety kills or otherwise disrupts the invasive cells (i.e., microbes and/or spermatozoa).

The NO-donor moieties suitable for use in the present invention must be capable of being attached, preferably covalently, to the vector delivery component and of releasing NO during use. Suitable NO-donor moieties can be derived from nitrate esters, furoxans, ketoximes, S-nitrosothiols, nitrosohydrazines, hydroxylamides, and the like. Of course, other NO-donor moieties can be used if desired so long as they meet the conditions required for the present invention.

Nitrate esters may release NO by several routes, such as, for example, $$RONO_2 + 2e^- + H^+ \rightarrow ROH + NO_2^-$$
$$NO_2^- + e^- + H^+ \rightarrow HO^- + NO$$
$$NO_2^- + M^{n+} \rightarrow M^{(n+1)} + O + NO$$

where R is an alkyl group preferably having 2 to 8 carbon atoms, and more preferably 2 to 6 carbon atoms, and $M^{n+}$ is a metal ion (e.g., $Fe^{2+}$, $Cu^+$, $Cr^{2+}$, $Co^{2+}$, and the like. NO may also be released from such nitrate esters by a thiol-activated scheme:

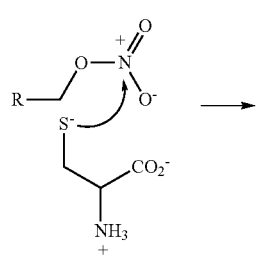

-continued

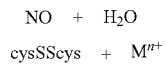

NO + $H_2O$
cysSScys + $M^{n+}$

Furoxans may also release NO via a thiol-activated scheme, as illustrated below (using 1,2,5-oxiadiazole-2-oxide as an example):

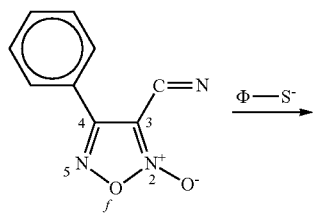

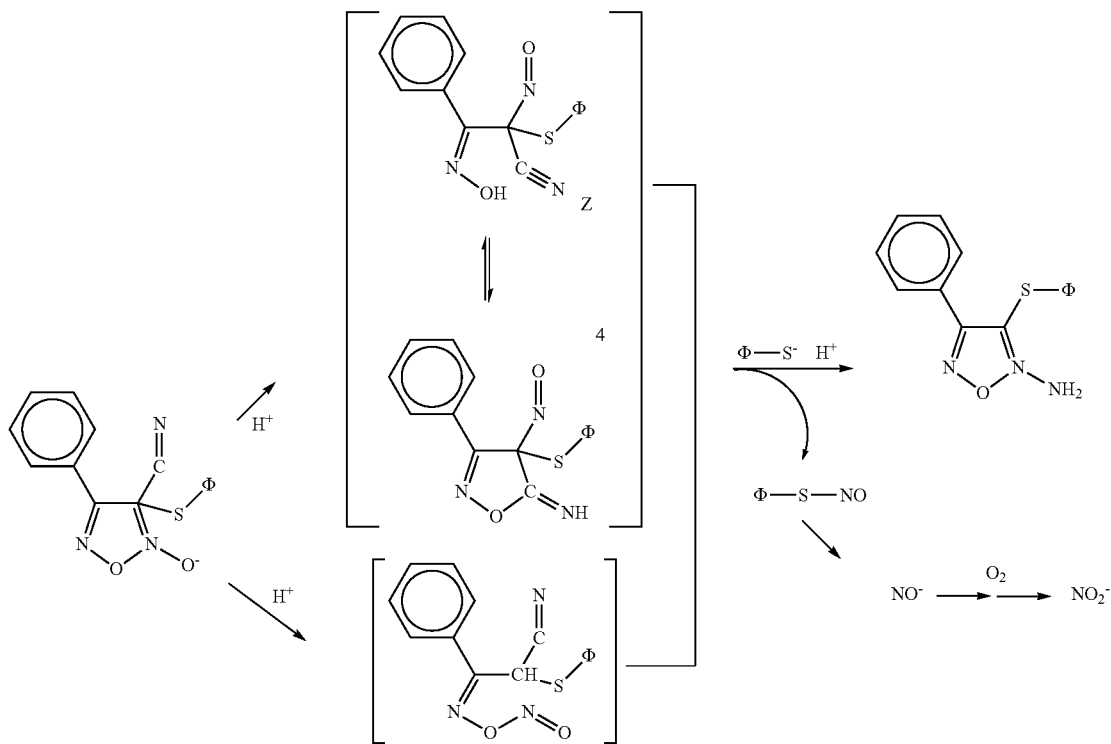

Conjugated ketoximes, using (±)-E-4-ethyl-2-[(E)-hydroxyimino]-5 nitro-3-hexenamide (NOR-3) as an example, can release NO via the following scheme:

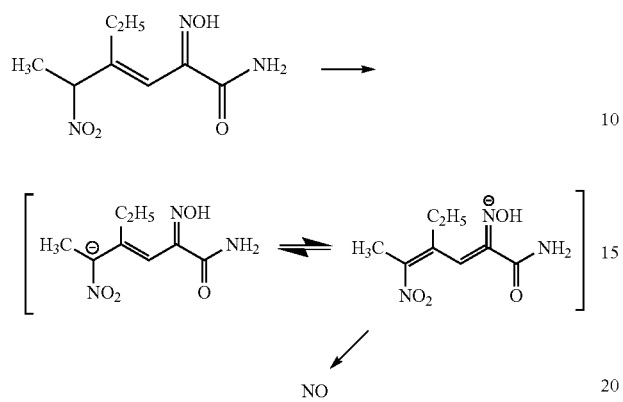

NOR-3 (0.5 mM in 0.1 M PBS) has a half-life of about 30 minutes at pH 7.4 and 37° C. Likewise, imines can also be used as NO-donor moieties. For example, 3-(4-morpholinyl) sydnomine (SIN-1) can release NO through the following reaction scheme:

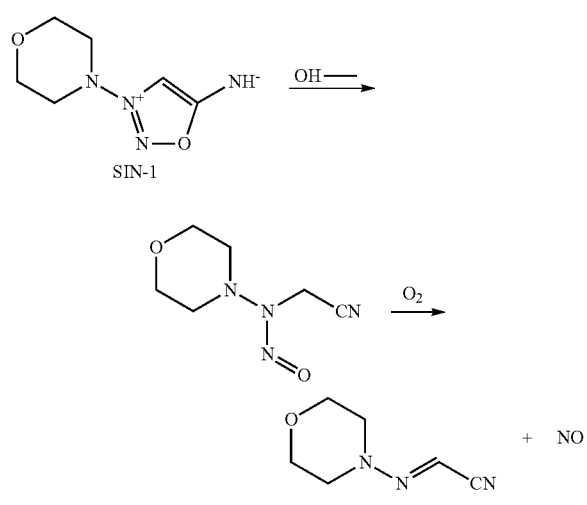

S-nitrosothiols, as shown below for S-nitroso-N-acetyl-penicillamine (SNAP) and S-nitrosoglutathione, can also produce NO:

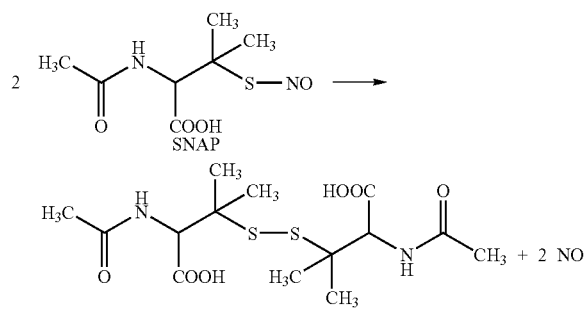

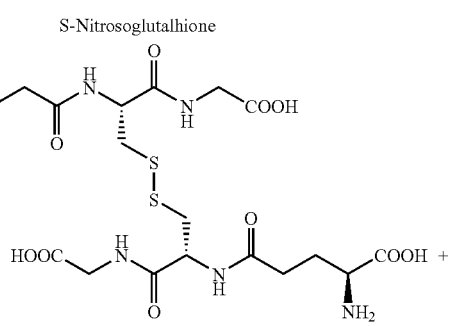

NO can also be released from 2-nitroso hydrazine derivatives, including diazeniumdiolates, such as 1-hydroxy-2-oxo-3-(3-aminopropyl)-3-isopropyl-1-triazene (NOC-5) and 1-hydroxy-2-oxo-3-(N-3-methyl-aminopropyl)-3-methyl-1-triazene (NOC-7), as indicated below:

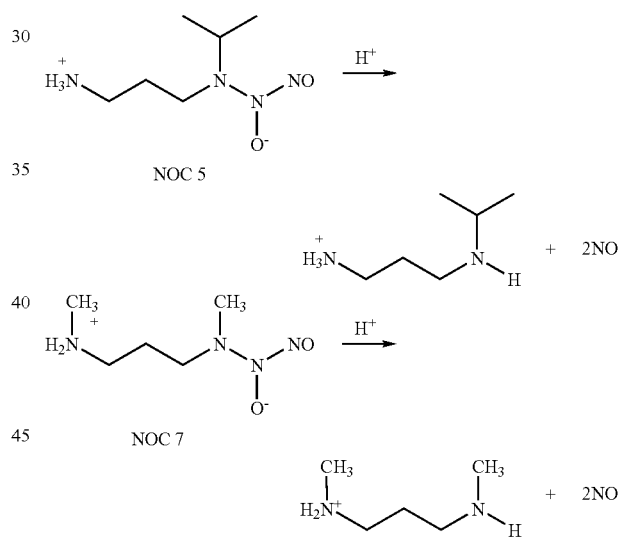

(Z)-1-{N-[3-Aminopropyl]-N-[4-(3-aminopropylammonio)butyl]-amino}-diazen-1-ium-1,2-diolate] (shown below; spermine-NONOate) is thought to release NO by a similar mechanism:

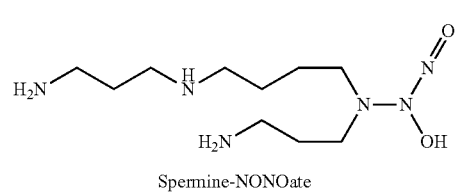 [SMILES: NCCCNCCCCN(CCCN)N(O)N=O]

Hydroxylamides can also be used as the NO-donor moieties. For example, hydroxyurea reacts with hemoglobin to produce iron nitrosyl hemoglobin, nitrite, and nitrate, thereby releasing NO. Hydroxyurea can also release NO via the peroxidase-mediated hydrolysis of hydroxyurea to hydroxylamine.

For contraceptive antimicrobial activity, the vector can be any compound that blocks spermatozoal binding to the oocyte or is otherwise contraceptive (a surrogate marker for this activity is the ability of the vector to induce premature acrosomal loss in vitro) and blocks microbial binding to the target (host) cells. By itself, it should have contraceptive and antimicrobial activities. Specifically, the vector should be an adhesin antagonist (receptor analog). General examples include polyanionic polymers and/or oligomers with affinity for adhesins that bind to heparan sulfate or other glycosaminoglycans. Examples within this class include cellulose sulfate, polystyrene sulfonate, dextran sulfate, naphthalenesulfonic acid polymer (e.g., Pro2000; Indevus Pharmaceuticals, Lexington, Miss.), polymethylene hydroquinone sulfonic acid, or sulfuric acid modified mandelic acid (SAMMA). These agents have activities against HIV-1, HSV-1, HSV-2, *Chlamydia trachomatis*, and *Neisseria gonorrhoeae*. Based on adhesin receptor specificities, other pathogens that should be affected by these agents and NO, include *Streptococcus* spp (see, e.g., Puliti et al., "Inhibition of nitric oxide synthase exacerbates group B *streptococcus* sepsis and arthritis in mice," Inf. Immun. 72: 4891-4 (2004); Kerr et al., "Nitric oxide exerts distinct effects in local and systemic infections with *Streptococcus pneumoniae*," Microb. Pathogen. 36: 303-10 (2004); Ozturk et al., "Serum and mucosal nitric oxide levels and efficacy of sodium nitroprusside in experimentally induced acute sinusitis," Yonsei. Med. J. 44: 424-8 (2003); Leib et al., "Inducible nitric oxide synthase and the effect of aminoguanidine in experimental neonatal meningitis," J. Inf. Dis. 177: 692-700 (1998)), *Staphylococcus* spp (Nablo et al., "Nitric oxide-releasing sol-gels as antibacterial coatings for orthopedic implants," Biomaterials 26: 917-24 (2005); Zhang et al., "Differential antibacterial activity of nitric oxide from the immunological isozyme of nitric oxide synthase transduced into endothelial cells," Nitric Oxide 7: 42-9 (2002)), *Mycoplasma* spp (Hickman-Davis et al., "Cyclophosphamide decreases nitrotyrosine formation and inhibits nitric oxide production by alveolar macrophages in mycoplasmosis," Inf. Immun. 69: 6401-10 (2001); Hickman-Davis et al., "Surfactant protein A mediates mycoplasmacidal activity of alveolar macrophages by production of peroxynitrite," Proc. Nat. Acad. Sci. USA 96: 4953-8 (1999)), *Mycobacterium* spp (Smeulders et al., "S-Nitrosoglutathione cytotoxicity to *Mycobacterium smegmatis* and its use to isolate stationary phase survival mutants," FEMS Microbiol. Lett. 239: 221-8 (2004)), *Mycoplasma* spp (Bogdan, "Reactive oxygen and reactive nitrogen metabolites as effector molecules against infectious pathogens," in *The innate immune response to infection* (Kaufmann et al., eds.), Washington, D.C.: ASM Press, p. 357-96 (2004)), *Listeria monocytogenes* (Carryn et al., "Impairment of growth of *Listeria monocytogenes* in THP-1 macrophages by granulocyte macrophage colony-stimulating factor: release of tumor necrosis factor-alpha and nitric oxide," J. Inf. Dis. 189: 2101-9 (2004); Myers et al., "Localized reactive oxygen and nitrogen intermediates inhibit escape of *Listeria monocytogenes* from vacuoles in activated macrophages," J. Immunol. 171: 5447-53 (2003); Remer et al., "Nitric oxide is protective in listeric meningoencephalitis of rats," Inf. Immun. 69: 4086-93 (2001)), *Helicobacter pylori* (Bussiere et al., "Spermine causes loss of innate immune response to *Helicobacter pylori* by inhibition of inducible nitric-oxide synthase translation," J. Biol. Chem. 280: 2409-12 (2005); Potter et al., "Exogenous nitric oxide inhibits apoptosis in guinea pig gastric mucous cells," Gut 46: 156-62 2000;), *Borrelia* spp (Lusitani et al., "*Borrelia burgdorferi* are susceptible to killing by a variety of human polymorphonuclear leukocyte components," J. Infect. Dis. 185: 797-804 (2002)), and *Bordella pertussis* (Canthaboo et al., "Investigation of role of nitric oxide in protection from *Bordetella pertussis* respiratory challenge," Infect. Immun. 70: 679-84 (2002); Torre et al., "Regulation of inflammatory responses to *Bordetella pertussis* by N(G)-monomethyl-L-arginine in mice intranasally infected," Mediat. Inflam. 8: 25-9 (1999)). Table 1 below provides a summary of examples of contraceptive antimicrobial vector/NO donor combinations for use in the present invention.

For non-contraceptive antimicrobial activity, the vector should antagonize microbial adhesin binding to target cells. The targeted microbe should be sensitive to NO. For example, fibronectin antagonists (Ofek et al., "Adhesins, receptors, and target substrata involved in the adhesion of pathogenic bacteria to host cells and tissues," in *Bacterial adhesion to animal cells and tissues*, Washington, D.C.: ASM Press, p. 177-405 (2003)) and NO are effective against *Borrelia* spp (Lusitani et al., "*Borrelia burgdorferi* are susceptible to killing by a variety of human polymorphonuclear leukocyte components," J. Infect. Dis. 185: 797-804 (2002)), *Chlamydia trachomatis* (Chen et al., "Nitric oxide production: a mechanism of *Chlamydia trachomatis* inhibition in interferon-gamma-treated RAW264.7 cells," FEMS Immunol. Med. Microbiol. 14: 109-20 (1996); Azenabor et al., "*Chlamydia pneumoniae* survival in macrophages is regulated by free $Ca^{2+}$ dependent reactive nitrogen and oxygen species," J. Infect. 46: 120-8 (2003); Igietseme "Molecular mechanism of T-cell control of *Chlamydia* in mice: role of nitric oxide in vivo," Immunology 88: 1-5 (1996); Igietseme et al., "Inhibition of intracellular multiplication of human strains of *Chlamydia trachomatis* by nitric oxide," Biochem. Biophys. Res. Commun. 232: 595-601 (1997)), *Streptococcus* spp (Puliti et al., "Inhibition of nitric oxide synthase exacerbates group B *streptococcus* sepsis and arthritis in mice," Infect. Immun. 72: 4891-4 (2004); Kerr et al., "Nitric oxide exerts distinct effects in local and systemic infections with *Streptococcus pneumoniae*," Microb. Pathogen. 36: 303-10 (2004)), *Fusobacterium nucleatum* (Allaker et al., "Antimicrobial effect of acidified nitrite on periodontal bacteria," Oral Microbiol. Immunol. 16: 253-6 (2001)), *Mycobacterium* spp (Bogdan, "Reactive oxygen and reactive nitrogen metabolites as effector molecules against infectious pathogens," in *The innate immune response to infection* (Kaufmann et al., eds.), Washington, D.C.: ASM Press, p. 357-96 (2004); Yamashiro et al., "Lower expression of Th1-related cytokines and inducible nitric oxide synthase in mice with streptozotocin-induced diabetes mellitus infected with *Mycobacterium tuberculosis*," Clin. Exp. Immunol. 139: 57-64 (2005); Copenhaver et al., "A mutant of *Mycobacterium tuberculosis* H37Rv that lacks expression of antigen 85A is attenuated in mice but retains vaccinogenic potential," Infect. Immun. 72: 7084-95 2004)), *Porphyromonas gingivalis* (Bogdan, "Reactive oxygen and reactive nitrogen metabolites as effector molecules against infectious pathogens," in *The innate immune response to infection* (Kaufmann et al., eds.), Washington, D.C.: ASM Press, p. 357-96 (2004)), *Salmonella enterica* (Bogdan, "Reactive oxygen and reactive nitrogen metabolites as effector molecules against infectious pathogens," in *The innate immune response to infection* (Kaufmann et al., eds.), Washington, D.C.: ASM Press, p. 357-96 (2004)), *Staphylococcus* spp (Nablo et al., "Nitric oxide-releasing sol-gels as antibacterial coatings for orthopedic implants," Biomaterials 26: 917-24 (2005); Zhang et al., "Differential antibacterial activity of nitric oxide from the immunological isozyme of nitric oxide synthase transduced into endothelial cells," Nitric Oxide 7: 42-9 (2002)), and *Yersinia* spp (Dykhuizen et al., "Antimicrobial effect of acidified nitrite on gut pathogens: importance of dietary nitrate in host defense," Antimicrob. Agents Chemother. 40: 1422-5 (1996); Campos-Perez et al., "Toxicity of nitric oxide and peroxynitrite to bacterial pathogens of fish," Dis. Aquat. Org. 43: 109-15 (2000)), as well as the parasites *Trichomonas vaginalis* (Crouch et al., "Binding of fibronectin by *Trichomonas vaginalis* is influenced by iron and calcium," Microb. Pathogen. 31: 131-44 (2001); Gradoni et al., "Nitric oxide and anti-protozoan chemotherapy," Parassitologia. 46: 101-3 (2004)) and *Leishmania* spp (Bogdan, "Reactive oxygen and reactive nitrogen metabolites as effector molecules against infectious pathogens," in *The innate immune response to infection* (Kaufmann et al., eds.), Washington, D.C.: ASM Press, p. 357-96 (2004)). Table 2 below provides a summary of examples of non-contraceptive antimicrobial vector/NO donor combinations suitable for use in the present invention.

Other suitable adhesin receptor antagonists include, for example, lactosyl- and galactosylceramides, laminin fragments, peptidoglycans, and glycopeptides. (See, e.g., Ofek et al., "Adhesins, receptors, and target substrata involved in the adhesion of pathogenic bacteria to host cells and tissues," in *Bacterial adhesion to animal cells and tissues*, Washington, D.C.: ASM Press, p. 177-405 (2003).)

TABLE 1

Contraceptive antimicrobial vectors for enhancement by nitric oxide: target microbes

| Adhesin/adhesion molecule specificity | Vector | Microbe | Nitric oxide effect |
|---|---|---|---|
| heparan sulfate, heparin and other sulfated glycosaminoglycans; sulfated sugars; sulfated polysaccharides; glycosaminoglycans; hyaluronan; sulfomucin; sulfated glycoprotein; sulfated glycolipids; sulfated glycoconjugates; sulfated proteoglycans | cellulose sulfate; polystyrene sulfonate; dextran sulfate; SAMMA; polymethylenehydroquinone sulfonate | HIV | NO donors inhibit HIV-1 reverse transcriptase; protective effect of NO on CNS after HIV infection |
| | | HSV | NOS inhibitors increase viral titers in mice; NO inhibits viral replication |
| | | *Chlamydia* spp | NO donors inhibit *C. trachomatis* replication; NOS inhibitors increase bacterial titers in mice |
| | | *Bordetella pertussis* | NO (iNOS) protects mice against *Bordetella pertussis* infection and decreases mortality to *Bordetella pertussis* infection in vivo |
| | | *Borrelia* spp | NO kills *Borrelia* in vitro |
| | | *Helicobacter pylori* | NO contributes to killing *H. pylori* in macrophages and protects gastric cells from *H. pylori*-induced apoptosis |
| | | *Listeria monocytogenes* | NO contributes to impairment of intracellular growth of *L. monocytogenes*, retention of *L. monocytogenes* by activated macrophages and protects against listeric meningoencephalitis in rats |
| | | *Mycobacterium* spp | Bactericidal action of NO donor against *M. smegmatis* |
| | | *Mycoplasma* spp | iNOS-deficient mice have higher titers than controls after infection with *M. pulmonis* |
| | | *Streptococcus* spp | mortality of mice infected with Group B *streptococcus* increased by NOS inhibitor; protective effect of NO against GBS-induced meningitis in rats; direct inhibition of *S. pneumoniae* by NO and NO donor |
| | | *Staphylococcus* spp | NO donors and NOS-derived NO kill Staph and protect against Staph infections |
| | | *Plasmodium falciparum* (protozoon) | control of infection in human tissue by NO-mediated mechanisms |
| | | *Trypanosoma* spp (protozoon) | intracellular and extracellular morphotypes of *Trypanosoma* killed by NO in vitro and in vivo |
| | | *Leishmania* spp (protozoon) | NO produced by macrophages kills intracellular *Leishmania* |
| | | Giardia (protozoon) | parasitostatic effect of NO donors |

TABLE 2

Noncontraceptive antimicrobial vectors for enhancement by nitric oxide: target microbes

| Adhesin/adhesion molecule specificity | Vector | Microbe | Nitric oxide effect |
|---|---|---|---|
| Fibronectin | Fibronectin fragments (e.g., peptides 4-15 residues in length that contain the recognition sequence Arg-Gly-Asp or Arg-X-Asp-Ser or Leu-Ile-Gly-Arg-Lys-Lys) | *Borrelia* spp | NO inhibits Borrelia |
| | | *Chlamydia trachomatis* | inhibition by macrophages antagonized and bacterial titer in mice increased by NOS inhibitors; replication inhibited by NO donors |
| | | *Streptococcus* spp | NOS inhibitors increase mortality of infected mice; inhibition by NO donors |
| | | *Fusobacterium nucleatum* | bactericidal effect of nitrite (potential NO precursor) |
| | | *Mycobacterium* spp | NO contributes to pathogen control; reduced NO production in diabetics impairs defense against *M. tuberculosis*; inhibited NO donors |
| | | *Porphyromonas gingivalis* | NO contributes to pathogen control |
| | | *Salmonella enterica* | NO is essential for pathogen control |
| | | *Yersinia* spp | bactericidal effects of acidified nitrite; inhibited by NO donors |
| | | *Leishmania* (protozoon) | NO is essential for pathogen control |
| | | *Naegleria fowleri* | NO and/or NO donors kill *Naegleria* |

Although not wishing to be limited by theory, it appears that NO-couplings to produce the agents in the present invention will also improve the safety profile of vector units such as SAMMA, sulfonated hesperidins, phosphorylated hesperidins, polystyrene sulfonate, cellulose sulfate and the like, intended for use to prevent HIV infection. This is thought to be due primarily to the fact that NO donors inhibit production and actions of pro-inflammatory cytokines.

Concerns have been expressed regarding the ability of microbicides to increase production of inflammatory cytokines, which can cause proliferation of target cells for HIV infection (Keller et al., "Rigorous pre-clinical evaluation of topical microbicides to prevent transmission of human immunodeficiency virus," J. Antimicrob. Chemother. 51: 1099-1102 (2003); Keller et al., "Topical microbicides for the prevention of genital herpes infection," J. Antimicrob. Chemother. 55: 420-423 (2005); Stone, "Microbicides: a new approach to preventing HIV and other sexually transmitted infections," Nature Reviews 1: 977-85 (2002)). NO donors as provided by the present invention are thought to be beneficial in this context. NO donors either reduce production of inflammatory cytokines or reduce their actions. The extent of these actions is at least partially dependent upon the cell type and level of NO (Proud, "Nitric oxide and the common cold," Cur. Opin. Allergy Clin. Immunol. 5: 37-42 (2005)).

Vaginal application of the NO donor isosorbide mononitrate to women has no effect on the production of interleukin (IL)-1, IL-6, IL-8, IL-10, IL-15, tumor necrosis factor (TNF)-$\alpha$, or monocyte chemoattractant protein-1 (Ledingham et al., "Nitric oxide donors stimulate prostaglandin F(2 alpha) and inhibit thromboxane B(2) production in the human cervix during the first trimester of pregnancy," Mol. Hum. Reprod. 5: 973-982 (1999)). On the other hand, molsidomine, a precursor to the NO donor SIN-1, decreases levels of the pro-inflammatory cytokines TNF-$\alpha$, IL-1 beta and IFN-gamma and increases production of the anti-inflammatory cytokines IL-6 and IL-10 in ischemic renal cells (Rodriguez-Pena et al., "Intrarenal administration of molsidomine, a molecule releasing nitric oxide, reduces renal ischemia-reperfusion injury in rats," Amer. J. Transplant. 4: 1605-1613 (2004)). Similar beneficial effects of this NO donor have been seen in rats with experimental allergic encephalomyelitis (Kwak et al., "Molsidomine ameliorates experimental allergic encephalomyelitis in Lewis rats," Immunopharmacol. Immunotoxicol. 25: 41-52 (2003)).

The NO donor SNAP decreases production of the pro-inflammatory cytokine, IL-12, in mouse macrophages (Xiong et al., "Inhibition of interleukin-12 p40 transcription and NF-kappaB activation by nitric oxide in murine macrophages and dendritic cells," J. Biol. Chem. 279: 10776-10783 (2004)). Similar inhibitory activity is seen in human peripheral blood mononuclear cells (Rachlis et al., "Nitric oxide reduces bacterial superantigen-immune cell activation and consequent epithelial abnormalities," J. Leukocyte Biol. 72: 339-346 (2002)), in activated human pulmonary microvascular endothelial cells (Jiang et al., "Effects of antioxidants and NO on TNF-alpha-induced adhesion molecule expression in human pulmonary microvascular endothelial cells," Resp. Med. 99: 580-91 (2005)), rat basophilic leukemia cells (Heywood et al., "Nicorandil inhibits degranulation and TNF-alpha release from RBL-2H3 cells," Inflam. Res. 51: 176-181 (2002)), colonic tissue from colitic (induced colitis) mice (Salas et al., "Nitric oxide supplementation ameliorates dextran sulfate sodium-induced colitis in mice," Lab. Invest. 82: 597-607 (2002)) and in lipopolysaccharide (LPS)-induced airway inflammation in mice (Lagente et al., "A nitric oxide-releasing salbutamol elicits potent relaxant and anti-inflammatory activities," J. Pharmacol. Exp. Ther. 310: 367-375 (2004).

The NO donor NOC-18 reduces the number of IFN-gamma-secreting CD4+T cells in patients with unstable angina and coronary spastic angina (Soejima et al., "Preference toward a T-helper type 1 response in patients with coronary spastic angina," Circulation 107: 2196-2200 (2003)), and the NO donor nitroprusside decreases production of pro-inflammatory cytokines after reperfusion in coronary artery bypass graft (Freyholdt et al., "Beneficial effect of sodium nitroprusside after coronary artery bypass surgery: pump function correlates inversely with cardiac release of proinflammatory cytokines," J. Cardiovasc. Pharmacol. 42: 372-378 (2003)). NO donors inhibit stimulus-induced increases in pro-inflammatory cytokines, while having little effect on resting levels.

NO produced in response to IL-1$\beta$ and TNF-$\alpha$ stimulation causes increased cyclooxygenase 2 (COX-2) expression in mesangial cells. However, NO donors decrease COX-2 in these cells, likely through feedback inhibition (Diaz-Cazorla et al., "Dual effect of nitric oxide donors on cyclooxygenase-2 expression in human mesangial cells," J. Amer. Soc. Nephrol. 10: 943-952 (1999)). NO donors exert feedback inhibition on NO production in response to inflammatory cytokines and LPS (Galley et al., "Regulation of nitric oxide synthase activity in cultured human endothelial cells: effect of antioxidants," Free Rad. Biol. Med. 21: 97-101 (1996)). IL-1 beta-stimulated chondrocytes show increased activation of NFkappaB, an effect that is abrogated by the NO donor S nitrosocysteine ethyl ester (Clancy et al., "Nitric oxide sustains nuclear factor kappaB activation in cytokine-stimulated chondrocytes," Osteoarthrit. Cartil. 12: 552-558 (2004)). Similar effects are noted in human mesangial cells (Diaz-Cazorla et al., "Dual effect of nitric oxide donors on cyclooxygenase-2 expression in human mesangial cells," J. Amer. Soc. Nephrol. 10: 943-952 (1999)) and in mouse macrophages (Xiong et al., "Inhibition of interleukin-12 p40 transcription and NF-kappaB activation by nitric oxide in murine macrophages and dendritic cells," J. Biol. Chem. 279: 10776-10783 (2004)). Pretreatment of human mesangial cells with the NO donors SIN-1 or nitroprusside decreases the subsequent increase in NFkappaB binding and macrophage chemoattractant protein-1 (MCP-1) expression in response to TNF-$\alpha$ or IL-1$\beta$ (Lee et al., "Exogenous nitric oxide inhibits tumor necrosis factor-alpha- or interleukin-1-beta-induced monocyte chemoattractant protein-1 expression in human mesangial cells. Role of IkappaB-alpha and cyclic GMP," Nephron 92: 780-787 (2002)). Increased permeability of microvessels making up the blood-brain barrier in response to IL-1$\beta$, IFN-$\gamma$, and LPS is reversed by NO donors (Wong et al., "Cytokines, nitric oxide, and cGMP modulate the permeability of an in vitro model of the human blood-brain barrier," Exp. Neurol. 190: 446-455 (2004)). Further, NO donors promote apoptosis of activated macrophages (Niinobu et al., "Negative feedback regulation of activated macrophages via Fas-mediated apoptosis," Amer. J. Physiol. 279: C504-0509 (2000)), which are targets for HIV infection. This effect may depend on the NO donor concentration (and by inference, the NO concentration) used (von Knethen et al., "NF-kappaB and AP-1 activation by nitric oxide attenuated apoptotic cell death in RAW 264.7 macrophages," Mol. Biol. Cell 10: 361-372 (1999)). Proliferation of T- and other immune cells and their recruitment in response to TNF-$\alpha$, IL-2 or LPS is substantially reduced by several NO donors (Corinti et al., "Regulatory role of nitric oxide on monocyte-derived dendritic cell functions," J. Interfer. Cytokine Res. 23: 423-431 (2003); Haider et al., "Dual functionality of cyclooxygenase-2 as a regulator of tumor necrosis factor-mediated G1 shortening and nitric oxide-mediated inhibition of vascular smooth muscle cell proliferation," Circulation 108: 1015-1021 (2003); Macphail et al., "Nitric oxide regulation of human peripheral blood mononuclear cells: critical time dependence and selectivity for cytokine versus chemokine expression," J. Immunol. 171: 4809-4815 (2003)).

The above findings suggest that incorporation of an NO donor into a topical microbicide as provided by this invention may, among other effects, improve its safety profile. NO donors inhibit the production and actions of inflammatory cytokines that may act to proliferate target cells for HIV infection.

The synthesis of the NO donor/vector adduct of the adhesin receptor antagonist can be achieved by standard organic synthetic pathways, in which the NO donor moiety is attached to a spacer molecule (e.g., alkane of 2-8 carbons in length) that contains a moiety suitable for coupling to the vector (e.g., amino, carboxyl, or hydroxyl). The spacer molecule containing the NO donor can be linked to hydroxyl, amino or carboxyl moieties of the vector via an ester or amide linkage. In instances where the vector contains polyol groupings (e.g., dextran or cellulose derivatives), regioselective attachment of the NO donor as a nitrate ester can be effected. Representative examples of such synthetic methods are presented below; of course, other methods can be used to prepare the NO donor/vector adducts of this invention.

Nitrate esters of SAMMA. Reaction of the bromoalkanols in anhydrous acetonitrile with silver nitrate affords the required nitrooxy-alkanols as shown in Equation 1 for bromalkanols ranging in size from C2 to C6.

Eq 1

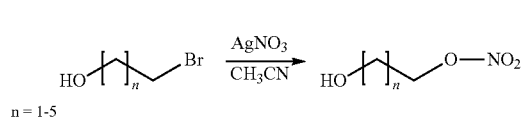

n = 1-5

Of course, values of n greater than 5 can be used if desired for the nitrate esters in Equations 1-4. As shown in Equation 2, substoichiometric coupling to SAMMA free acid is accomplished with 1,1'-carbonyldiimidazole (CDI) in dry DMF linking the nitrooxy alkanol (1,3-nitrooxyphenol) by an ester linkage. (Endres et al., "NO-donors, part 3: nitrooxyacylated thiosalicylates and salicylates—synthesis and biological activities," Eur. J. Med. Chem. 34: 895-901 (1999).)

Eq 2

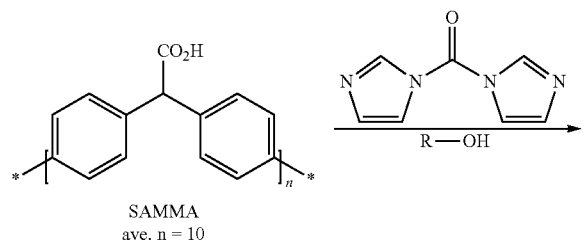

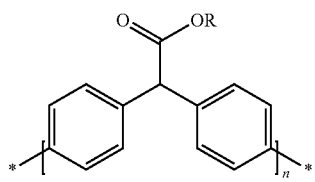

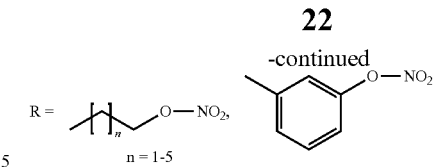

n = 1-5

A series of nitrooxyalkyl amines C2-C8 can be prepared, that can be coupled to SAMMA by an amide linkage. Focus is placed on the C3 adduct at levels of substitution from 5-60%. Minin and Walton ("Radical Ring Closures of 4-Isocyanato Carbon-Centered Radicals," J. Org. Chem. 68: 2960-3 (2003)) have described the synthesis of 4-bromo-1-butylamine hydrobromide by refluxing 4-amino-1-butanol in concentrated hydrobromic acid; this can be applied to prepare other bromo-alkylamine hydrobromides. As shown in Equation 3, reaction of the bromo-alkylamine hydrobromides with 2 equivalents of silver bromide in dry acetonitrile gives the nitrooxy-alkylamines (as their ammonium nitrate salts).

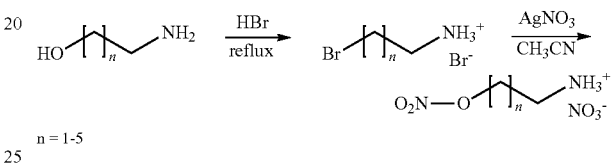

n = 1-5

Treatment of the amine salts with one equivalent of imidazole in dry DMF provides the free amine necessary for CDI coupling to SAMMA as shown in Equation 4.

Eq 4

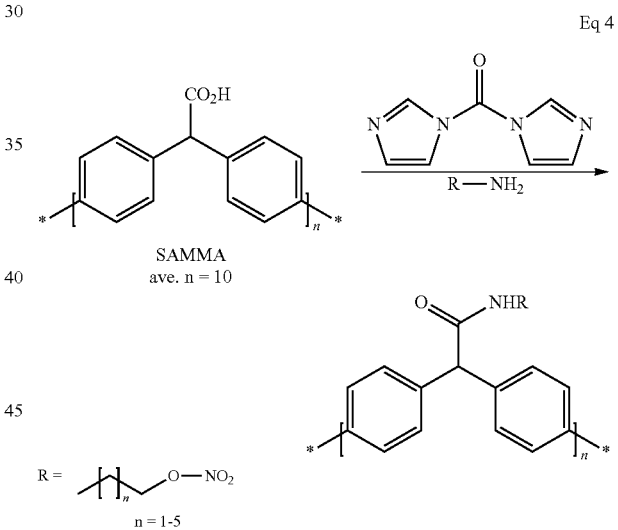

n = 1-5

Furoxan Derivatives of SAMMA. Furoxan derivatives (furazan oxide, 1,2,5-oxadiazole 2-oxide) release NO in the presence of thiol cofactors. (Medana et al., "Furoxans as Nitric Oxide Donors. 4-Phenyl-3-furoxancarbonitrile: Thiol-Mediated Nitric Oxide Release and Biological Evaluation," J. Med. Chem. 37: 4412-6 (1994); Ferioli et al., "A new class of furoxan derivatives as NO donors: mechanism of action and biological activity," J. Pharmacol. 114: 816-20 (1995); Schonafinger, "Heterocyclic NO prodrugs," Farmaco. 54: 316-20 (1999).) Among other therapeutic activities, furoxan derivatives inhibit HIV-1 reverse transcriptase. (Persichini, et al., "Nitric oxide inhibits the HIV-1 reverse transcriptase activity," Biochem. Biophys. Res. Commun. 258: 624-7 (1999).) Furoxans that can be linked to SAMMA are prepared with commercially available starting materials. Nitromethane and sodium methoxide are combined in dry DMF followed by the addition of sodium benzene sulfinate and iodine to form phenyl nitromethyl sulfone (PNS). As shown in Equation 5, PNS is cyclized by heating in glacial acetic acid-nitric acid for 1 hour at 65° C. (Kelley et al., "Synthesis of bis(arylsulfonyl) furoxans from aryl nitromethyl sulfones," J. Heterocycl. Chem. 14: 1415-6 (1977).)

Eq 5

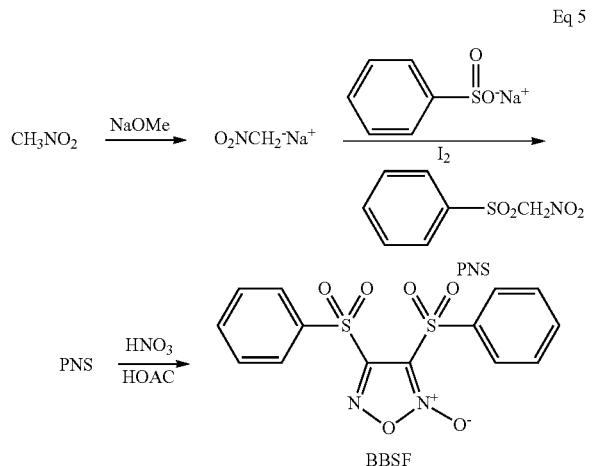

BBSF

The 3,4-bis(benzene sulfonyl) furoxan (BBSF) reacts with alcohols under alkaline conditions to afford substituted furoxans. (Sorba et al., "Unsymmetrically substituted furoxans. Part 16. Reaction of benzenesulfonyl substituted furoxans with ethanol and ethanethiol in basic medium," J. Heterocycl. Chem. 33: 327-34 (1996); Lolli et al., "A new class of ibuprofen derivatives with reduced gastrotoxicity," J. Med. Chem. 44: 3463-8 (2001).) As shown in Equation 6, treatment of BBSF with 1,3-propanediol in THF with 50% NaOH leads to displacement of one sulfone group.

Eq 6

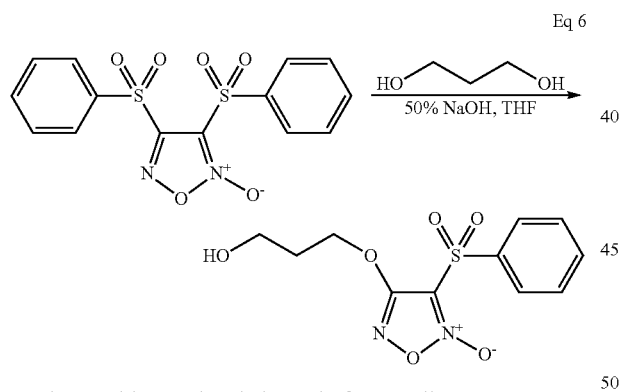

The resulting molecule is ready for coupling to SAMMA. Similarly, treatment of BBSF with ethanol then 1,3-propanediol forms the ethoxy derivative as indicated in Equation 7. (Sorba et al., "Unsymmetrically substituted furoxans. Part 16. Reaction of benzenesulfonyl substituted furoxans with ethanol and ethanethiol in basic medium," J. Heterocycl. Chem. 33: 327-34 (1996).)

Eq 7

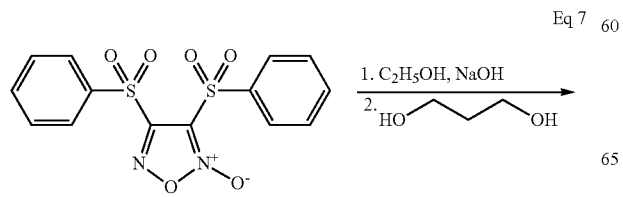

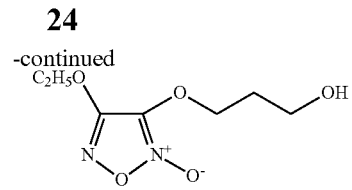

Another furoxan can be prepared by the reaction of crotonaldehyde with $NaNO_2$ in acetic acid yielding 3-methyl-4-furoxancarbaldehyde (Fruttero et al., "Unsymmetrically substituted furoxans. Part 11. Methylfuroxan-carbaldehydes," J. Heterocycl. Chem. 26: 1345-7 (1989)) which is reduced, as shown in Equation 8, to 3-methyl-4-furoxanmethanol with $NaBH_4$ in dioxane. (Di Stilo et al., "New 1,4-Dihydropyridines Conjugated to Furoxanyl Moieties, Endowed with Both Nitric Oxide-like and Calcium Channel Antagonist Vasodilator Activities," J. Med. Chem. 41: 5393-401 (1998).)

Eq 8

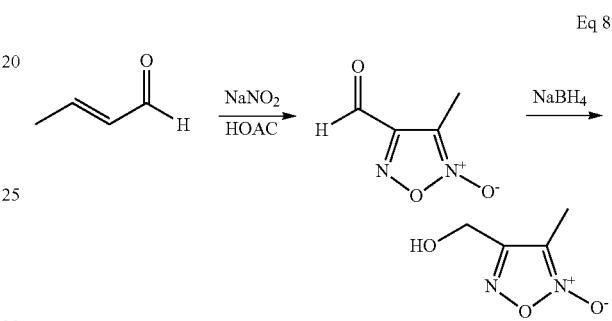

These can be coupled to SAM MA at different levels of substitution (e.g., 5 to 60%).

Nitrated cellulose sulfate. Nitrate ester derivatives of cellulose sulfate can be prepared by regioselective sulfation of cellulose or cellulose derivative (e.g., acetate, trimethysilyl ether, nitro, nitrito or tosylate) on C2 and C3, followed by nitration at C1, as shown below:

Possible reaction pathways for regioselective sulfation of cellulose and its derivatives

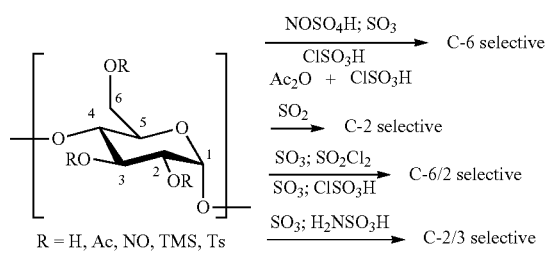

The reaction shown below provides good selectivity at C-6.

Possible reaction pathways for nitration of cellulose and its derivatives

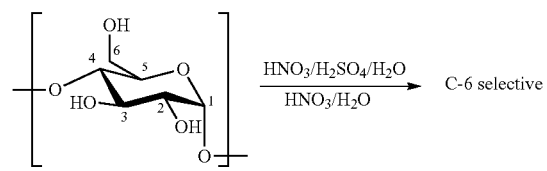

The amount of nitrating product can be controlled by reaction temperature and reaction time.

The method of the present invention is carried out by applying an effective amount of the NO-coupled anti-microbial agent or agents of this invention to the area or areas expected to undergo sexual contact during the sexual activity, especially to those areas in which the transmission of STD-causing organisms is more likely and which will likely be in contact with a partner's bodily fluids which may contain the STD-causing organisms. For purposes of this invention, an "effective amount" is an amount sufficient to inactivate, but not necessarily kill, STD-causing organisms on contact and/or upon release of nitric oxide. Suitable NO-coupled anti-microbial agent or agents for use in the present invention include, for example, phosphorylated hesperidins coupled with a NO-donor, sulfonated hesperidins coupled with a NO-donor, polystyrene sulfonates coupled with a NO-donor, substituted benzenesulfonic acid formaldehyde co-polymers coupled with a NO-donor, $H_2SO_4$-modified mandelic acids coupled with a NO-donor, cellulose sulfates coupled with a NO-donor, and the like. As indicated above, preferred anti-microbial agents for use in this invention include $H_2SO_4$-modified mandelic acids (SAMMAs) coupled with a NO-donor (i.e., NO-SAMMAs).

Generally, the NO-coupled anti-microbial agent or agents are incorporated into conventional carriers, such as, for example, lotions, creams, jellies, liniments, ointments, salves, oils, foams, gels, washes, suppositories, slow-releasing polymers, coatings, or devices, and the like so that they can be easily applied topically in the present methods. The carriers may also include other ingredients such as, for example, pH modifiers, stabilizers, buffers, surfactants, moisturizers, colorants, thickeners, flavorings, fragrances, perfumes, and the like. The inhibitory agents of the present invention may also be used with conventional birth-control or safe-sex devices. For example, the NO-coupled anti-microbial agent or agents could be incorporated into or simply used in conjunction with condoms (i.e., via lubricants applied to the interior and/or exterior surfaces), diaphragms, cervix caps, or similar products. The NO-coupled anti-microbial agent or agents of the present invention could also, for example, be released into the vagina (or rectum in the case of anal intercourse) by hand, via suppositories, or by using conventional tampon or syringe techniques. The method of administering or delivering the NO-coupled anti-microbial agent or agents to the potential STD-transmission site is not critical so long as an effective amount of the NO-coupled anti-microbial agent is delivered to the site in a timely manner. Preferably the formulations and/or method of delivering the NO-coupled anti-microbial agent or agents allows the inhibitory agents to remain in the appropriate area during (and even after) the sexual activity in order to maximize the effectiveness.

Preferred inhibitory agents (i.e., the anti-microbial component of the NO-coupled anti-microbial agents) include phosphorylated hesperidins, sulfonated hesperidins, polystyrene sulfonates, substituted benzenesulfonic acid formaldehyde co-polymers, $H_2SO_4$-modified mandelic acids, and cellulose sulfates. Preferably the inhibitory agents, as well as the NO-coupled anti-microbial agents, used are water soluble or dispersable (or at least partially so). Generally, the NO-coupled anti-microbial agents are employed at a concentration of about 0.2 mg/g or higher in a suitable formulation, preferably at a concentration of about 10 mg/g to about 100 mg/g, and more preferably at a concentration of about 20 mg/g to about 70 mg/g based on the total weight of inert and active ingredients. Although it is generally preferred that such anti-STD compounds be used at non-cytotoxic levels in order to minimize potential side effects, these compounds can also be used, if desired, at levels at which the STD-organisms (or a significant portion thereof) are effectively killed rather than simply inactivated or inhibited.

In actual use, the NO-coupled anti-microbial agent in a suitable carrier or vehicle is applied, preferably topically, to the general area or areas of expected sexual contact (e.g., areas in which bodily fluids are likely to be generated and/or deposited) prior to the sexual activity. For vaginal heterosexual intercourse, the NO-coupled anti-microbial agents could be inserted into the vagina prior to intercourse. For anal intercourse (heterosexual or homosexual), the NO-coupled anti-microbial agents could be inserted into the rectum prior to intercourse. For either vaginal or anal intercourse, the NO-coupled anti-microbial agents could be incorporated into the lubricant used with the condom. For added protection it is generally preferred that the NO-coupled anti-microbial agent be applied before intercourse or other sexual activity and that, if appropriate, a condom be used. For even further protection, the NO-coupled anti-microbial agents can be reapplied after completion of the sexual activity; in such cases, a douche or rinse with the NO-coupled anti-microbial agent in a liquid carrier solution could be used. Using edible carriers and suitable flavorings, the NO-coupled anti-microbial agents could also be used to provide protection during oral sex (heterosexual or homosexual); a mouthwash containing NO-coupled anti-microbial agents could be used afterwards. By incorporating desirable flavorants, scents, fragrances, and colorants, the NO-coupled anti-microbial agents could become a "pleasing" or "desirable" component of the sexual activity (i.e., a sex aid or toy) thereby increasing the probability of their use and, therefore, the degree of protection afforded the sexual parties.

One advantage of the present method is that it can be used for protection during a wide variety of sexual activities (vaginal, anal, or oral) by heterosexuals, bisexuals, and homosexuals of either gender. Another advantage of the present method of reducing the transmission of STDs is that this method can be implemented and/or used by either party. Thus, a woman could use the present method to protect herself (as well as her partner) with or without the partner's knowledge of the method being used. Moreover, one partner would not be required to rely on his or her partner's claim of being STD-free or agreement to use condoms or other barrier devices for protection. Either or both sexual parties could initiate and implement the use of the present method prior to, or after, the sexual encounter. Preferably the method is used before the sexual activity and most preferably both before and after the sexual activity. Although use only after the sexual activity would provide less protection, it would still be desirable to implement this method afterwards if the method was not used prior to the sexual activity for any reason (e.g., in cases of rape). Of course, the sooner this method is initiated after the sexual activity the better. Preferably the method is initiated within one hour, more preferably within 15 minutes, and most preferably almost immediately after the sexual activity. Even after periods greater than these, however, the use of this method as soon as possible after the sexual activity may provide at least some protection (as compared to no treatment).

Still another advantage of the present invention is that, in contrast to other contraceptive or protective methods which rely on a cytotoxic compound (e.g., nonoxynol-9), the NO-coupled anti-microbial agents used in this invention do not significantly affect or inhibit the growth characteristics of the normal vaginal flora or otherwise significantly irritate the vaginal tissue when used at inhibitory, noncytotoxic, or clinical concentrations. Thus, the beneficial components of normal vaginal flora are not disrupted by the use of the present invention. Significant inhibition or modifications of the vaginal flora or other irritations (such as when nonoxynol-9 is used) can lead to increased risks of infections (both STD and non-STD types), unusual discharges, general discomforts, and the like, which, in turn, can lead to a reluctance to use or fully take advantage of the protective method. Such inhibition or modifications of the vaginal flora, irritation of vaginal tissue, and/or lesions can actually increase the risk of STD transmission and infection. By avoiding or reducing the intensity of these effects, the present method is more likely to be used on a consistent basis. By reducing the number of unprotected sex acts (preferably to zero) and encouraging the use of the methods of this invention both before and after each sex act, the overall degree of protection should be significantly increased. By avoiding or reducing vaginal irritations and especially lesions on the vaginal walls (or rectum lining in the case of anal intercourse), the transmission of STD should be further reduced since transmission of STD-causing organisms is generally easier where damage to the cell walls has occurred. Thus, improvements in ease of use, reduction in side effects, the ability to be initiated by either party, and the ability to be used for different and varied sexual activities give the present invention a significant advantage as a contraceptive and/or as an anti-STD method.

The present NO-coupled anti-microbial agents can also be used by persons who are not at risk or significant risk of pregnancy. For purposes of this application, the phrases "not at risk for pregnancy" or "not at significant risk for pregnancy" are intended to include individuals who, for any number of reasons, are not capable of becoming pregnant or who are employing alternative birth control methods. Such individuals not capable of becoming pregnant include, for example, homosexual partners, men in general, diagnosed sterile individuals (including women regardless of the cause of sterility and men who are unable to impregnate a woman regardless of the cause of sterility), post-menopause women, and the like. Individuals who are employing alternative birth control methods, for purposes of this application, are not at significant risk of pregnancy. For example, a woman using a contraceptive pill and/or condom would not be considered to be at risk for pregnancy even though the effectiveness of the pill and/or condom is not 100 percent; similarly, users of other conventional birth control methods would not be considered to be "at significant risk of pregnancy" even though the failure rate may be higher than that for the pill and/or condom. For purposes of this specification, the phrase "not at risk of pregnancy" is also intended to also include the phrase "not at significant risk of pregnancy" as that term is used above.

All references (including patents, patent publications, and other publications) are incorporated by references in their entireties. Unless otherwise noted, all percentages and ratios in the present specification are based on weight.

EXAMPLES

Example 1

NO7-SAMMA. This example illustrates the preparation of anti-microbial agents wherein the delivery vector is derived from SAMMA and the nitric oxide donor moiety is derived from nitrooxypropanol. In this example, the anti-microbial agent is about 7% substituted with the nitric oxide donor moiety.

The NO-donor (3-nitrooxy-1-propanol) was synthesized by reacting silver nitrate with 3-bromo-1-propanol in acetonitrile. Silver nitrate (18.7 g, 110 mmoles) was dissolved in acetonitrile (200 mL). 3-Bromo-1-propanol (18.9 g; 100 mmoles) dissolved in 25 mL acetonitrile was added. The reaction flask was protected from light using aluminum foil. The reaction mixture was stirred at ambient temperatures for about 96 hours; after 2 hours, a yellow precipitate (AgBr) was observed. The reaction mixture was filtered through a cellite pad to remove particulate AgBr. The solvent was removed using rotary evaporation to yield a yellow oil which was dissolved in dichloromethane. The resulting solution was extracted with saturated NaCl in water to remove residual silver as AgCl and then dried over anhydrous sodium sulfate. After removal of the solvent by rotary evaporation and then distillation at about 50 mm Hg, 3-nitrooxy-1-propanol, a clear yellow oil, was obtained in about 62 percent yield. Identity was confirmed using IR and $^{13}$C NMR.

NO-SAMMA was prepared using essentially the reaction scheme shown in Equation 2 above. SAMMA (10.02 g; 74.8 acid meq; prepared as described in Example 4 of U.S. Pat. No. 5,932,619) was dissolved in 100 mL dimethylformamide (DMF) in a flask equipped with a drying tube to maintain low moisture levels and then cooled to 0° C. using an ice bath. A sub-stoichiometric amount of 1,1'-carbonyldiimidazole (CDI; 4.02 g; 24.8 mmoles; coupling agent) was dissolved in 40 mL dry DMF and added dropwise over 40 minutes to the stirred SAMMA solution. The reaction was continued for an additional 45 minutes with stirring at 0° C. Nitrooxypropanol (2.74 g; 22.6 mmoles) in 20 mL dry DMF was added dropwise over a 30 minute period during which time the reaction temperature was allowed to rise to ambient temperature. The reaction was continued for about 4 hours with stirring at ambient temperature. The reaction mixture was decanted into 1500 mL water and then acidified to pH 1.9 using 6N HCl. The resulting light pink precipitate was suction filtered, washed with water (500 and 250 mL portions), and suction filtered. The wet precipitate was dried by lyophilization to yield 10.15 g of NO7-SAMMA (salmon-colored powder) in about 97 percent yield.

Example 2

NO23-SAMMA. This example illustrates the preparation of anti-microbial agents wherein the delivery vector is derived from SAMMA and the nitric oxide donor moiety is derived from nitrooxypropanol. In this example, however, the anti-microbial agent is approximately 23 percent substituted with the nitric oxide donor moiety.

SAMMA (3.19 g; 23.8 acid meq; prepared as described in Example 4 of U.S. Pat. No. 5,932,619) was dissolved in 500 mL dry DMF in a flask equipped with a drying tube to maintain low moisture levels and then cooled to 0° C. using an ice bath. An excess amount of 1,1'-carbonyldiimidazole (CDI; 9.73 g; 60 mmoles; coupling agent) was dissolved in 40 mL dry DMF and added to the stirred SAMMA solution. After a further addition of 30 mL dry DMF, the reaction was continued for an additional 45 minutes with stirring at 0° C. Nitrooxypropanol (0.86 g; 7.1 mmoles; from Example 1) in 5 mL dry DMF was added dropwise over a 2 minute period. The reaction temperature was allowed to rise to ambient temperature. The reaction was continued for about 15 hours with stirring at ambient temperature. The reaction mixture was decanted into 1000 mL water and then acidified to pH 1.6 using 6N HCl. The resulting deep red precipitate was suction filtered, washed with water (two 200 mL portions), and suction filtered. The wet precipitate was dried by lyophilization to yield 2.78 g of NO23-SAMMA in about 73 percent yield.

Example 3

Effect of NO-SAMMA on acrosomal loss (AL). Both NO7-SAMMA (Example 1) and NO23-SAMMA (Example 2) were evaluated for their effect on acrosomal loss.

Measurement of AL was carried out as described previously. (Anderson et al., "Preclinical evaluation of sodium cellulose sulfate (Ushercell™) as a contraceptive antimicrobial agent," J. Androl. 23: 426-38 (2002); Zaneveld et al., "Use of mandelic acid condensation polymer (SAMMA), a new antimicrobial contraceptive agent, for vaginal prophylaxis," Fert. Steril. 78: 1107-15 ((2002).) Fresh human semen was collected from healthy donors by self-masturbation. All samples were used within one hour of collection. Spermatozoa were isolated and washed by centrifugation through buffered Ficoll and resuspension in BWW medium. A sample was withdrawn for motility assessment, and the sperm suspensions' were treated with either SAMMA, 3-nitrooxypropan-1-ol, NO7-SAMMA, or NO23-SAMMA. The concentrations of SAMMA and nitrooxypropanol were equivalent to the concentrations of these moieties found in either 0.075 µg/mL N07-SAMMA or 0.02 µg/mL NO23-SAMMA, based on their respective degrees of substitution. Reaction induced by 0.075 µg/mL NO7-SAMMA was compared to the reactions induced by either 0.072 µg/mL SAMMA or 0.037 µM nitrooxypropanol, and to the predicted response to the two agents added in combination, assuming independence of action. Similarly, reaction induced by 0.02 µg/mL NO23-SAMMA was compared to the reactions induced by either 0.019 µg/mL SAMMA or 0.0364 µM nitrooxypropanol. All reactions were carried out in either the presence or absence of added extracellular $Ca^{2+}$ (1.28 mM). Fifteen minutes after adding either SAMMA, nitrooxypropanol, NO7-SAMMA or NO23-SAMMA, sperm motility was measured and spermatozoa were fixed in buffered glutaraldehyde, air-dried onto slides, stained with Bismark Brown Y and Rose Bengal and scored for the presence of acrosomes (De Jonge et al., "Synchronous assay for human sperm capacitation and the acrosome reaction," J. Androl. 10: 232-39 (1989)). Data are expressed as the average % maximal response, based on the AL induced by a maximally stimulating concentration of the calcium ionophore A23187.

Both NO7-SAMMA and NO23-SAMMA induced AL in the absence of added extracellular $Ca^{2+}$. The response to 0.075 µg/mL N07-SAMMA in the absence of added $Ca^{2+}$ (41% maximal loss) was over 6-fold higher than the predicted response to an equivalent amount of the NO donor from which NO7-SAMMA was derived. In the presence of $Ca^{2+}$, the response to NO7-SAMMA was synergistic over the predicted response to combined addition of equivalent concentrations of NO donor and SAMMA. The increase in AL in the presence of NO7-SAMMA, as shown in FIG. 1, was nearly 5.6-fold than the predicted increase in NO donor-induced AL due to the addition of SAMMA.

Even higher activity, see FIG. 1, was observed with NO23-SAMMA. The response to 0.02 µg/mL NO23-SAMMA in the absence of added $Ca^{2+}$ (about 47% maximal loss) was 6.6-fold higher than the predicted response to an equivalent amount of the NO donor from which NO23-SAMMA was derived. The observed synergy in this instance was approximately the same as that observed for NO7-SAMMA, but the concentration required for the effect is only 27% of that required for NO7-SAMMA, likely due to increased level of substitution on NO donor. The increase in AL in the presence of NO23-SAMMA was nearly 21.5-fold higher than the predicted increase in NO donor-induced AL due to the addition of SAMMA. As shown in FIG. 2, the $ED_{50}$ values of fractionated NO23-SAMMA (0.09 ng/mL; see Example 5 for details regarding fractionation) and unfractionated NO23-SAMMA (8 ng/mL) are more than 2800 and 30 times, respectively, less than the $ED_{50}$ for SAMMA (250 ng/mL).

Example 4

Effect of NO-SAMMA against *C. trachomatis*. Infection of HeLa cells by *C. trachomatis* (serotype E/UW-5/CX) was measured as described by Cooper et al. ("*Chlamydia trachomatis* infection of human fallopian tube organ cultures," J. Gen. Microbiol. 136: 1109-15 (1990)) in the presence and absence of NO7-SAMMA, SAMMA, or nitrooxypropanol. Approximately $1\times10^5$ IFU/mL of chlamydial elementary bodies were added to different concentrations of either SAMMA or NO7-SAMMA, from 50 µg/mL to 500 µg/mL, and incubated at 0° C. for four hours, after which the mixture was inoculated onto HeLa cell monolayers. In separate experiments, HeLa cell monolayers were incubated with either SAMMA or NO7-SAMMA at different concentrations, ranging from 50-500 µg/mL at 37° C. for one hour, after which the overlaying medium was decanted and the monolayer was washed with fresh medium without microbicide. This was followed by inoculation of the monolayer with chlamydial elementary bodies. One hour after inoculation, free microbes and/or microbicide were removed by washing, and the HeLa cell cultures were incubated for an additional 48 hours at 37° C. *Chlamydia*-induced inclusions were measured by immunofluorescence, after reacting cultures with Kalisted chlamydia culture confirmation fluorescein-conjugated monoclonal antibody. Data are expressed as bacterial titer (IFU/mL) at each concentration of either SAMMA or NO7-SAM MA.

A 3-log reduction of *C. trachomatis* occurred at a NO7-SAMMA concentration that is approximately one order of magnitude lower than for SAMMA (see FIG. 3; 3-log reduction for SAMMA alone was at 20 mg/mL as compared to 1.9 mg/mL for NO7-SAMMA). Further, the inhibitory effect of NO7-SAMMA, unlike that of SAM MA, occurred not only at the level of direct effect on the elementary body, but also on the target (HeLa) cells (see FIG. 4); an $IC_{50}$ of 0.7 mg/mL was found for NO7-SAMMA. Interestingly, the inhibitory effect of nitroprusside against *C. trachomatis* ($IC_{50}$=23 µM) was about the same as that against spermatozoa (74% maximal AL at 22 µM), suggesting that *C. trachomatis* and spermatozoa may have similar sensitivity to NO.

Example 5

Fractioned NO23-SAMMA. This example illustrates the preparation and evaluation of an anti-microbial agent, wherein the delivery vector is derived from SAMMA that has been fractionated on silica gel to achieve a more narrow range of molecular weights, and the nitric oxide donor moiety is derived from nitrooxypropanol. This fractionated material is distinguished from that described in Example 2 wherein non-fractionated (bulk) SAMMA was used as the delivery vector. In this example, the anti-microbial agent is approximately 23 percent substituted with the nitric oxide donor moiety. This fractionated material exhibited unexpectedly increased activity as compared to the unfractionated material.

SAMMA (3.0 g; 22.4 acid meq, prepared as described in Example 4 of U.S. Pat. No. 5,932,619) was dissolved in a minimal volume (9 mL) of methanol. This solution was applied to a 200×35 mm glass column filled ⅔ with chromatographic silica gel, 100-200 mesh (Fisher Scientific), equilibrated with methylene chloride and topped with washed sand, and eluted (200 mL each) with a discontinuous gradient of methylene chloride containing increasing concentrations of methanol (2%, 10%, 20%, 30% 100%, v/v; increasing polarity). Fractions of 200 mL were collected. Fractionated SAMMA (to be used for the preparation of fractionated NO23-SAMMA) was recovered in the 30% methanol (20-30% fraction) elution. Yield: 2.55 g (85%). MALDI TOF MS showed a predominant molecular weight distribution of the fractionated SAMMA between 700-2500, with molecular weight <600 representing a minor (approx. 2-3%) constituent, and very low (<1%) amounts with molecular weight equal to or greater than 2500. The 20-30% fraction was used to prepare fractionated NO23-SAMMA using the procedure described in Example 2 for NO23-SAMMA.

Fractionated NO23-SAMMA has the highest activity as a stimulus of acrosomal loss of any the compounds studied (see FIG. 2). Covalent modification of SAMMA having a more clearly defined range of molecular weights increased efficacy by about two orders of magnitude over NO23-SAMMA. SAMMA fractionated on silica gel is similar to unfractionated (bulk) SAMMA as a stimulus of AL (68% maximal AL at 0.25 µg/mL, essentially the same $ED_{50}$ as for unfractionated SAMMA). Although this represents a synergistic response to equivalent concentrations of either nitrooxypropanol or SAMMA added alone (separately), synergism cannot be quantified for fractionated NO23-SAMMA, since equivalent concentrations of SAMMA and NO donor are so low as to produce responses below the limit of detection. The $ED_{50}$ of fractionated NO23-SAMMA is 0.09 ng/mL. This quantity of fractionated NO23-SAMMA contains the equivalent of 0.08 ng/mL SAMMA and 0.13 nM nitrooxypropanol; it, however, represents an increased activity over SAMMA of nearly 2.800-fold. For comparison, the $ED_{50}$ of NO23-SAMMA (8 ng/mL) contains the equivalent of 6.8 ng/mL SAMMA and 11.2 nM nitrooxypropanol. The $ED_{50}$ for nitrooxypropanol as a stimulus of acrosomal loss is 120 nM.

Fractionated NO23-SAMMA has essentially no effect (i.e., less than about 10% inhibition) on the percentage of motile spermatozoa at concentrations up to 10 mg/mL (Control motility=69.4±0.6 (SEM) %; motility with 10 mg/mL fractionated NO23-SAMMA=63.2±2.2%; N=4). These data show that NO-SAMMA has no effect on sperm viability.

Acrosomal loss induced by SAMMA is $Ca^{2+}$-dependent (Anderson et al., "SAMMA induces premature acrosomal loss by $Ca^{2+}$ signaling dysregulation", J. Androl. 27: 568-577 (2006)). Unless otherwise noted, acrosomal loss data were obtained from assays that included $Ca^{2+}$ in the extracellular medium. In contrast, acrosomal loss induced by NO donors occurs independent of $Ca^{2+}$. These properties can be exploited to determine the contributions of the SAMMA and NO donor moieties to acrosomal loss induced by NO-SAMMA. Although not wishing to be limited by theory, it appears that acrosomal loss in the presence of added extracellular $Ca^{2+}$ may be due to either or both moieties, whereas acrosomal loss in the absence of $Ca^{2+}$ is due entirely to the NO donor moiety.

Fractionated NO23-SAMMA induces acrosomal loss in the absence of $Ca^{2+}$ with an $ED_{50}$ of 0.37 ng/mL. Based on nitrogen content of fractionated NO23-SAMMA (1.98±0.106%), this is equivalent to 0.53 nM equivalents of nitric oxide donor (see FIG. 5). SAMMA at 0.25 µg/mL in the absence of $Ca^{2+}$ has essentially no effect (Anderson et al., "SAMMA induces premature acrosomal loss by $Ca^{2+}$ signaling dysregulation", J. Androl. 27: 568-577 (2006)), and the $ED_{50}$ for nitrooxypropanol is 0.12 µM ($Ca^{2+}$-independent). The effect is of fractionated NO23-SAMMA in the absence of $Ca^{2+}$ is likely due to the NO donor moiety of NO-SAMMA, and is clearly enhanced relative to effects of either SAMMA or NO donor added alone. Strictly speaking, this does not represent a synergistic response, since SAMMA is without effect in the absence of $Ca^{2+}$.

Contraception in rabbits by fractionated NO23-SAMMA is substantially more effective than contraception by SAMMA. Greater efficacy is seen at a fractionated NO-SAMMA concentration one order of magnitude lower than the concentration of SAMMA. Sperm pretreatment with 5 mg/mL SAMMA reduces fertilization. However, contraception of SAMMA is incomplete with 0.5 mg/mL SAMMA being essentially without effect. In contrast, 0.5 mg/mL fractionated NO23-SAMMA is essentially completely contraceptive; only 1 of 120 oocytes examined from 5 rabbits was fertilized. The contraceptive data, reported below, were obtained using washed rabbit spermatozoa incubated with the test compounds for about 15 minutes at 37° C. prior to insemination. About 22 to 34 million spermatozoa were used for fertilization testing. Oocytes were harvested about 25 to 27 hours post insemination and scored for fertilization. Average fertilization percentages per rabbit (along with 90% confidence limits) were as follows:

| Test Compound | Oocytes Examined (No. Of Rabbits Used) | % Fertilization (90% confidence limits)* |
|---|---|---|
| None (control) | 269 (12) | 90 (75.2-98.7)$^A$ |
| SAMMA (0.5 mg/mL) | 79 (3) | 78 (29.0-99.7)$^A$ |
| SAMMA (5 mg/mL) | 182 (7) | 7 (1.2-18.2)$^B$ |
| Fractionated NO23-SAMMA (0.5 mg/mL) | 120 (5) | 0.7 (0-6.8)$^C$ |

*Values with different superscript letter values are significantly different using Newman-Keuls multiple range test. A and B values are different at a p value <0.001; B and C values are different at a p value of 0.055.

Figure 6:
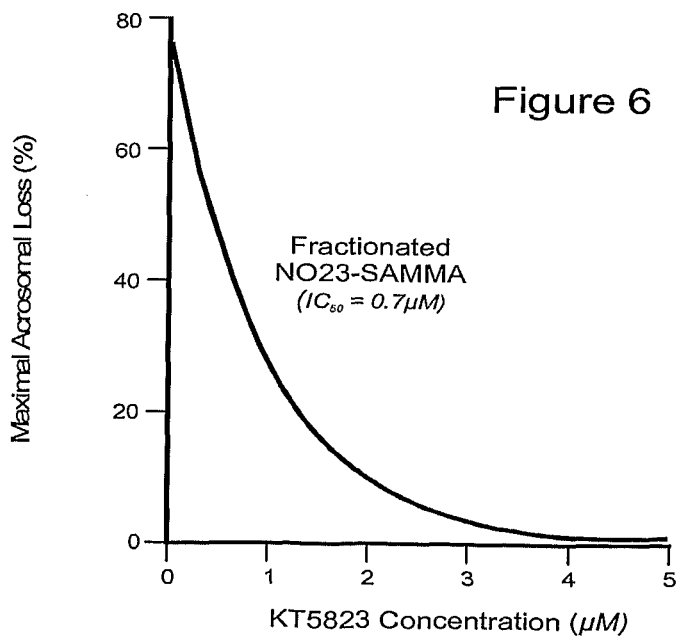
FIG. 6 illustrates the inhibition of acrosomal loss induced by fractionated NO23-SAMMA by selective protein kinase G inhibitor KT5823.

NO23-SAMMA, whether fractionated or not, appears, at least in part, to act through release of nitric oxide. Fractionated NO23-SAMMA-induced acrosomal loss in the absence of added extracellular $Ca^{2+}$ is inhibited by the selective protein kinase G inhibitor KT5823 (see FIG. 6). As noted above, SAMMA-induced acrosomal loss (SAL) is also inhibited by KT5823, as well as by nitric oxide synthase and guanylate cyclase inhibitors, suggesting a role of NO via the cGMP/protein kinase G pathway in this process. Acrosomal loss in human spermatozoa in response to NO donors is inhibited by protein kinase G inhibitors (Revelli et al., "Signaling pathway of nitric oxide-induced acrosome reaction in human spermatozoa", Biol. Reprod., 64: 1708-12 (2001)). SAMMA is ineffective in inducing acrosomal loss in the absence of added extracellular $Ca^{2+}$. By inference, acrosomal loss induced by fractionated NO23-SAMMA in the absence of added extracellular $Ca^{2+}$ is likely mediated by NO release from the NO donor moiety of fractionated NO23-SAMMA. Inhibition of acrosomal loss by the selective protein kinase G inhibitor supports this contention. The $IC_{50}$ for inhibition of fractionated NO23-SAMMA-induced acrosomal loss ($Ca^{2+}$-independent) by KT5823 is 0.7 µM (FIG. 6).

Fractionated NO23-SAMMA has activity against HIV and HSV. When direct comparisons are made, $IC_{50}$ values for NO-SAMMA are slightly higher than those for SAM MA. However, concentrations of fractionated NO-SAM MA required for 3-Log reduction in infectivity are lower than those for SAMMA. These results suggest that at higher concentrations, fractionated NO-SAMMA is more effective than SAMMA against HIV and HSV; the change in relative efficacy may reflect the contribution of nitric oxide release against these pathogens. HIV is sensitive to inhibition by the NO donor used to synthesize NO-SAMMA (nitrooxypropanol), although substantially less than to NO-SAMMA. Experiments were conducted to compare the activities of SAMMA and fractionated NO23-SAMMA against HIV-1 BaL infected primary lymphocytes. Host cells were inoculated with virus (200 TCID50/2×10$^5$ cells) for 2 h, and washed to remove unbound virus, before either SAMMA or fractionated NO23-SAMMA was added to the cultures. Viral replication was measured on day 7 of incubation (p24 levels). In all instances, viability of the target cells remained at approximately 98% for the duration of the experiments. These data are presented below.

| Compound | IC$_{50}$ (µg/mL) | 3-Log reduction (µg/mL) |
|---|---|---|
| SAMMA | 66 | 6560 |
| Fractionated NO23-SAMMA | 208 | 2084 |
| Nitrooxypropanol | 2544 | 1017 (80% reduction) |

SAMMA and fractionated NO23-SAMMA are highly active in preventing infection of lymphocytes by HIV-1 BaL. IC$_{50}$ values are less than 10 µg/mL. Fractionated NO23-SAMMA concentrations required to inhibit p24 values by 50% and 3-logs are about 3-fold lower than those for SAMMA. The dose-response for fractionated NO23-SAMMA between 1 µg/mL and 10 µg/mL is more responsive than that for SAMMA, suggesting involvement of the NO-SAMMA NO donor moiety. This possibility is likely, in view of possible reduced binding affinity of NO-SAMMA relative to SAMMA, due to reduced charge density of the NO donor adduct.

The ability of fractionated NO23-SAMMA to reduce infectivity of HSV-1 (F) and HSV-2 (G) was compared with the anti-HSV activities of the parent compound, SAMMA. Both agents are highly effective against these laboratory strains. In contrast to results obtained for HIV-1, IC$_{50}$ values are somewhat lower for SAMMA than for fractionated NO23-SAMMA. However, fractionated NO23-SAMMA is more effective in nearly completely inhibiting both viruses; 3-Log reductions are observed at NO-SAMMA concentrations that are 80% to 87% lower than SAMMA concentrations required for the same effect. Dose-responses for fractionated NO23-SAMMA are thus delayed, but sharper as compared with SAMMA. The slightly increased IC$_{50}$ values for fractionated NO23-SAMMA suggest increased sensitivity of HSV binding to changes in charge density caused by the covalent attachment of the NO donor moiety.

HSV Studies: One hour after adding serial 2-fold dilutions of either SAMMA or fractionated NO23-SAMMA to confluent human fibroblasts (foreskin) at concentrations ranging from 2 µg/mL to 256 µg/mL, cells were inoculated with either HSV-1 (F) or HSV-2 (G) (ATCC; MOI=0.05). After 48 hours (35° C., 5% CO$_2$), cells were visually examined for viral cytopathogenic effect (CPE) in the virus control wells. Cells were fixed and blocked (PBS with 0.2% BSA and 0.05% Tween 20). Viral titers were determined by ELISA, with HRP-conjugated polyclonal antibodies (Dako Corp, Carpinteria, Calif.). Reaction with 3,3',5,5'-tetramethylbenzidine (TMB) was measured spectrophotometrically (630 nm and 450 nm). Data were expressed as mean percentage of control viral incubations (±SEM) to which no microbicide was added.

HIV Studies: Primary lymphocytes and virus were incubated with microbicide (serial 10-fold dilutions, ranging from 1 ng/mL to 1 mg/mL) for 1 hour, followed by inoculation (50 TCID50/2×10$^5$ cells). After 2 hours, cells were washed to remove virus. Incubations continued with microbicide for 7 days, after which viral titers (p24) were measured. Data (pg/well) were expressed as mean±SEM of triplicate determinations. The data are consistent with activities of SAMMA and fractionated NO23-SAMMA in HIV-1 BaL-infected lymphocytes and suggest a greater contribution of the NO donor moiety of fractionated NO23-SAMMA at higher concentrations.

These data for both the HSV and HIV studies are presented below. The values for each dose-response curve includes the coefficient of determination ($r^2$), degrees of freedom (DoF), calculated concentration of inhibitor required to reduce viral titer by 50 percent (IC$_{50}$), and concentration of inhibitor to reduce viral titer by 99.9 percent (3-log).

| | SAMMA | | | Fractionated N023-SAMMA | | |
|---|---|---|---|---|---|---|
| | $r^2$ (DoF) | IC$_{50}$ (µg/mL) | 3-log (µg/mL) | $r^2$ (DoF) | IC$_{50}$ (µg/mL) | 3-log (µg/mL) |
| HIV-1 BaL | 0.9999 (6) | 6.5 | 60 | 0.9999 (6) | 2.5 | 23 |
| HSV-1 (F) | 0.9993 (6) | 7.8 | 214 | 1.0000 (6) | 22 | 42 |
| HSV-2 (G) | 0.994 (9) | 1.5 | 181 | 0.994 (7) | 5.2 | 24 |

Example 6

NO-SAM MA retains many biological properties of the parent compound, SAMMA, including the ability to inhibit hyaluronidase (a property believed to be responsible, in part, for some anti-microbial activity), and lack of effects on sperm motility and growth of lactobacilli (indicators of specificity of action and lack of general cytotoxic effects on spermatozoa and beneficial vaginal flora. See generally, Zaneveld et al. "Method for preventing sexually transmitted diseases," U.S. Pat. No. 5,932,619. This example evaluates some of these properties for fractionated NO23-SAMMA (prepared as in Example 5).

Hyaluronidase activity was measured as described in Example 8 of U.S. Pat. No. 5,932,619. Activity of fractionated NO23-SAMMA against hyaluronidase is very similar to that of SAMMA. In contrast, the NO donor moiety of NO23-SAMMA, nitrooxypropanol, is nearly without effect. The following results were obtained.

| Agent | IC$_{50}$ (µg/mL) | 3-Log reduction* (µg/mL) | Inhibition ± SEM (N = 4) |
|---|---|---|---|
| Fractionated NO23-SAMMA | 11.1 | 13.6 | 100 ± 2.0% at 15 µg/mL** |
| SAMMA | 8.1 | 14.9 | 104 ± 2.0% at 15 µg/mL |
| Nitrooxypropanol | — | — | 8 ± 1.8% at 50 µM |

*concentration required for 99.9% inhibition of activity
**15 µg/mL fractionated NO23-SAMMA contains 21.2 µM equivalent of nitrooxypropanol Sperm immobilization by fractionated NO23-SAMMA was evaluated by a modification (Anderson et al. "Evaluation of poly(styrene-4-sulfonate) as a preventive agent for conception and sexually transmitted diseases," J Androl 21:862-875 (2000)) of the method of Sander and Cramer ("A practical method for testing the spermicidal action of chemical contraceptives," Hum Fertil 6:134-137, 153 (1941)). Thirty seconds after adding different concentrations of the test agent (2.5 to 20 mg/mL for SAMMA and fractionated NO23-SAMMA and 1-10 mM for nitrooxypropanol), the fraction of motile spermatozoa was determined with brightfield microscopy (400×). Data are presented as the percentage of motile spermatozoa at each concentration of test agent. When possible, test outcomes were also reported as the concentration of agent in the semen sample that reduces motility by 50%.

Neither fractionated NO23-SAMMA, SAM MA, nor nitrooxypropanol can be regarded as spermicidal. Sperm motility is reduced by less than 10 percent by concentrations of these agents that are 4-8 orders of magnitude greater than concentrations required to induce acrosomal loss. The data are as follows.

| Test Agent | % Motile Spermatozoa (at 10 mg/mL test agent) av ± SEM (n = 4) | $IC_{50}$ |
| --- | --- | --- |
| None | 70 ± 0.6 | — |
| Fractionated NO23-SAMMA | 63 ± 2.2 at 10 mg/mL | 30 mg/mL |
| SAMMA | 67 ± 0.6 at 10 mg/mL | 64 mg/mL |
| Nitrooxypropanol | 66 ± 0.5 at 10 mM | 163 mM |

The effect of fractionated NO23-SAMMA on growth of *L. gasseri* was determined as described in Example 9 of U.S. Pat. No. 5,932,619. Similar to SAMMA, fractionated NO23-SAMMA has no effect on *lactobacillus* growth at concentrations up to 10 mg/mL. These data are shown below.

| Fractionated NO23-SAMMA (mg/mL) | Doubling Time (minutes) | Difference from Control (Confidence Level) |
| --- | --- | --- |
| 0 | 121.1 | — |
| 5.0 | 125.4 | >0.1 |
| 10.0 | 130.8 | >0.1 |

The release of nitric oxide from NO-SAMMA has been confirmed. Although available instrumentation lacked sensitivity to detect NO release in the biological systems that have been tested, chemical-induced release of NO from relatively high concentrations of NO-SAMMA could be quantified.

NO formation was measured by a modification of the method of Bertinaria et al. ("Synthesis and anti-*Helicobacter pylori* properties of NO-donor/metronidazole hybrids and related compounds," Drug Devel. Res. 60: 225-39, (2003). Fractionated NO23-SAMMA (0.1 mg/mL) was reacted with 50 mM cysteine in 50 mM sodium phosphate (pH 7.4 at 37° C.) for up to 24 hours. Equal volumes of reaction mixture and Griess reagent were reacted for 15 minutes and the absorbency at 540 nm was determined. Nitrite standards produced a linear standard curve ($r^2$=0.9999) in the range 1-50 μM, from which nitrite formation from nitrooxypropanol was measured. Higher concentrations could not be evaluated, since the pink/red reaction product when combined with the Griess reagent precipitated and could not be measured.

Nitrite formation (an indirect measure of NO formation) from fractionated NO23-SAMMA increased over time. The results are presented in FIG. 7. Nitrite formation when fitted to a kinetic curve showed first order sequential formation, A->B->C, which is similar to that describing nitrite formation from nitrooxypropanol.

The embodiments and examples described and discussed above are intended to illustrate the present invention and not to limit the scope of the invention which is defined in the appended claims.

That which is claimed is:

1. An anti-microbial agent for reducing risk of transmitting a sexually transmitted disease, said anti-microbial agent comprising:
   a covalent adduct of an $H_2SO_4$-modified mandelic acid and a nitric oxide donor,
   the nitric oxide donor consisting of a nitric oxide donor moiety and a spacer;
   the nitric oxide donor being covalently bonded through the spacer to a carbonyl carbon atom derived from a carboxyl of the $H_2SO_4$-modified mandelic acid wherein NO is released from the anti-microbial agent during use.

2. The anti-microbial agent as defined in claim 1, wherein the NO-donor is selected from the group consisting of nitrate esters, furoxans, ketoximes, S-nitrosothiols, nitrosohydrazines, and hydroxylamides.

3. The anti-microbial agent as defined in claim 1, wherein the NO-donor is a nitrate ester.

4. The anti-microbial agent as defined in claim 1, wherein the antimicrobial agent is contained in an inert carrier.

5. The anti-microbial agent as defined in claim 3, wherein the antimicrobial agent is contained in an inert carrier.

6. The anti-microbial agent as defined in claim 4, wherein the antimicrobial agent is at a concentration greater than about 0.2 mg/g.

7. The anti-microbial agent as defined in claim 5, wherein the antimicrobial agent is at a concentration greater than about 0.2 mg/g.

8. The anti-microbial agent as defined in claim 4, wherein the antimicrobial agent is at a concentration of about 10 to 100 mg/g.

9. The anti-microbial agent as defined in claim 5, wherein the antimicrobial agent is at a concentration of about 10 to 100 mg/g.

10. The anti-microbial agent as defined in claim 1, wherein the $H_2SO_4$-modified mandelic acid is a fractionated $H_2SO_4$-modified mandelic acid having a narrower molecular weight range and a higher biological activity relative to the $H_2SO_4$-modified mandelic acid without fractionation.

11. The anti-microbial agent of claim 1, wherein the covalent adduct of the $H_2SO_4$-modified mandelic acid and the nitric oxide donor is a compound having a structure:

wherein n is an average of 10 and the nitric oxide donor comprises a nitrate ester moiety; and
R at each monomer is independently H, —$(CH_2)_m$—O—$NO_2$ wherein m is 2-6 or 1,3-nitrooxyphenyl.

12. The anti-microbial agent of claim 11 wherein the the R's are each independently H or —$(CH_2)_3$—O—$NO_2$.

13. The anti-microbial agent of claim 11 wherein about 7% of the R's are $(CH_2)_3$—O—$NO_2$ and the remaining about 93% of the R's are H.

14. The anti-microbial agent of claim 11 wherein about 23% of the R's are $(CH_2)_3$—O—$NO_2$ and the remaining about 77% of the R's are H.

* * * * *